United States Patent [19]

Marrocco III et al.

[11] Patent Number: 5,723,573
[45] Date of Patent: Mar. 3, 1998

[54] THERMOSETTING POLYQUINOLINES

[75] Inventors: Matthew L. Marrocco III, Santa Ana; Lien-Chung Hsu, Glendale, both of Calif.

[73] Assignee: Hitachi Chemical Company, Ltd., Tokyo, Japan

[21] Appl. No.: 632,156

[22] Filed: Apr. 15, 1996

[51] Int. Cl.$^6$ .................................................. C08G 73/06
[52] U.S. Cl. .......................... 528/423; 528/125; 528/425; 528/495; 528/503; 521/28; 427/372.2; 427/407.01; 427/421; 264/239; 264/241
[58] Field of Search .................................. 528/125, 423, 528/503, 425, 495; 521/28; 427/407.1, 372.2, 407.01, 421; 264/239, 241

[56] References Cited

U.S. PATENT DOCUMENTS

| | | | |
|---|---|---|---|
| 3,756,982 | 9/1973 | Korshak | 268/41 R |
| 4,000,187 | 12/1976 | Stille | 260/50 |
| 4,507,462 | 3/1985 | Stille | 528/125 |
| 5,017,677 | 5/1991 | Stille | 528/125 |
| 5,247,050 | 9/1993 | Hendricks | 528/125 |

FOREIGN PATENT DOCUMENTS 9217516  10/1992  WIPO.

OTHER PUBLICATIONS

Baker, et al., "Hexaarylbenzene Units as Cross-Linking Sites for Polyquinolines," *Macromolecules*, vol. 12, No. 3, May–Jun. 1979, pp. 369–373.

Dirlikov, "Propargyl Thermosets, Coatings, and Fibers," *Polymer Preprints*, vol. 35, No. 1, Mar. 1994, pp. 339–340.

Hergenrother, et al., "Chemistry and Properties of Phenylethynyl Terminated Imide Oligomers and Their Cured Polymers," 39th International SAMPE Symposium, Apr. 11–14, 1994, pp. 961–968.

Stille, et al., "The Cross–Linking of Thermally Stable Aromatic Polymers by Aryl Cyanate Cyclotrimerization," *Macromolecules*, vol. 3, May–Jun. 1976, pp. 516–523.

Stille, "Polyquinolines," *Macromolecules*, vol. 14, No. 3, May–Jun. 1981, 870–880.

Sutherlin, et al., "Biphenylene–and Phenyl–End–Capped Oligomeric Polyquinolines Containing Acetylene Linkages: Preparation, Processing, and Composite Application," *Macromolecules*, vol. 19, No. 2, 1986, pp. 257–266.

Tani, "Oligomers and Polymers Containing Triple Bonds. Derivatives of Ethynylbiphenyl and Ethynylfluorene," *Bull. Chem. Soc. Jp.*, vol. 36, No. 4, 1963, pp. 391–396.

*Primary Examiner*—James J. Seidleck
*Assistant Examiner*—Duc Truong
*Attorney, Agent, or Firm*—Antonelli, Terry, Stout, & Kraus, LLP

[57] ABSTRACT

Thermosetting polyquinoline polymers, methods for preparing the polymers, and methods for curing the polymers are provided. The polymers incorporate quinoline repeat units and end groups which include a reactive acetylene functionality. On heat treatment, the reactive end groups form cross-links which render the polymer insoluble and extend the polymer's operating temperature.

34 Claims, 2 Drawing Sheets

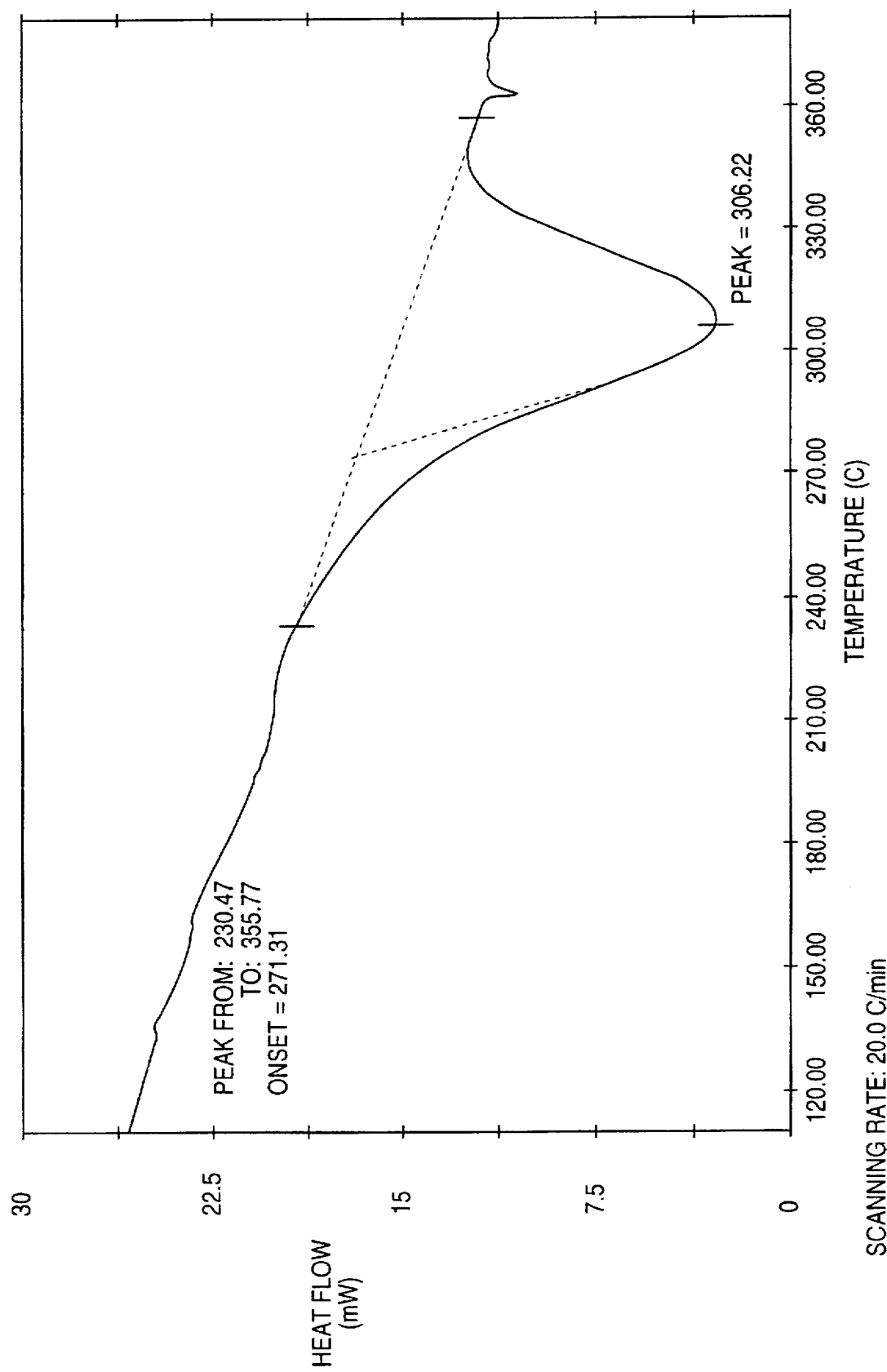

THERMOSETTING POLYQUINOLINES

FIELD OF THE INVENTION

This invention relates to novel polymer compositions comprising polyquinoline repeat units and reactive end groups, where the reactive end groups are capable of undergoing thermally activated cross-linking reactions to thereby provide a cross-linked polyquinoline product.

BACKGROUND OF THE INVENTION

Polyquinoline polymers which have excellent thermal stability and good mechanical properties are disclosed in U.S. Pat. No. 4,000,187 which issued to J. Stille on Dec. 28, 1976. The quinoline nucleus itself is thermally stable and resistant to oxidation and is, therefore, a good choice as a repeat unit for the design of high performance polymers. Such polyquinoline polymers may be prepared via the Friedlander condensation, as disclosed in the '187 patent, or by nucleophilic displacement polymerization, as disclosed in U.S. patent application Ser. No. 08/469,993, filed Jun. 6, 1995 by the Assignee of the present application. Other methods have also been used to prepare polyquinolines [e.g., Long Y. Chiang and John W. Swirczewski, *J. Chem. Soc., Chem. Commun.*, 1991, 131–132]. U.S. Pat. No. 4,000,187, application Ser. No. 08/469,993, and the Chiang et al article are fully incorporated herein by this reference.

The polyquinoline-forming polymerization reactions disclosed in the '187 patent and the '993 application are condensation-type reactions. Monomers used in such condensation polymerizations are generally characterized as AA, BB or AB monomers, where A and B represent complementary functional groups which can react to form polymer linkages. For example, when an AA and a BB monomer are reacted, the monomers react to form growing chains that may have either A or B ends. The polymer AA—BB—AA—BB—AA has A type ends, the polymer AA—BB—AA—BB has one A type end and one B type end, and the polymer BB—AA—BB—AA—BB has B type ends. If a type AB monomer is used, the polymer will have the following characteristic: AB—AB—AB—AB (one A type end and one B type end).

The polyquinoline homopolymers described in Assignee's '993 application are prepared either from two monomers, i.e., from a type AA monomer and a type BB monomer, or from a single type AB monomer. Polyquinoline copolymers are prepared from mixtures of (1) one type AB monomer with one or more additional type AB, AA or BB monomers, or (2) a type AA monomer and a type BB monomer with one or more additional type AA, BB or AB monomers.

Polyquinolines such as those produced in accordance with the Friedlander reaction disclosed in the '187 patent or the nucleophilic displacement reaction disclosed in the '993 application are useful as structural plastics that can withstand extreme environments, such as in high temperature coatings, as molding resins, and as composite matrix resins. Polyquinolines often have excellent electrical properties, including low dielectric constants, and low moisture absorption. Polyquinolines are therefore useful as electrical insulators, as for example in printed wiring boards, multichip modules, integrated circuits, electrical connectors, capacitors, wire coating and the like.

It has been recognized that for various uses it would be desirable to provide a polyquinoline polymer composition that could be cross-linked or thermoset. For example, as a matrix resin for composites, it is desirable to first form a prepreg consisting of fiber tow, tape or fabric, typically glass fibers or carbon fibers, coated with resin. The fibers may be coated by dipping into a solution or melt of the polymer resin. The prepreg is then "laid up," typically on a mold or form, and heat-treated to cause the polymer to flow and consolidate. It is often advantageous for the polymer to cross-link during the heat treatment so that it becomes resistant to further applications of heat or solvents. The composite may experience high-use temperatures, for example, as part of a supersonic aircraft wing or tail or as part of a printed circuit board which is subjected to soldering temperatures.

Some attempts have been made to prepare thermosetting polyquinolines, as in D. K. Sutherlin, J. K. Stille, and W. B. Alston, "Biphenylene and Phenyl-End-Capped Oligomeric Polyquinolines Containing Acetylene Linkages: Preparation, Processing and Composite Application," *Macromolecules*, 1986, 19, 257–266; U.S. Pat. No. 4,507, 462; J. K. Stille et al., "The Cross-Linking of Thermally Stable Aromatic Polymers by Aryl Cyanate Cyclotrimerization," *Macromolecules*, 1976, 9, 517–523; G. L. Baker et al., "Hexaarylbenzene Units as Cross-Linking Sites for Polyquinolines," *Macromolecules*, 1979, 12, 369–373. In some cases, rather exotic groups have been incorporated into the polyquinoline structure, for example biphenylene groups and hexaarylbenzene groups which would add considerably to the polymer cost. Earlier attempts to provide thermoset polymers with high thermal stability required the incorporation of cross-linking groups that required either a very high temperature cure, typically, at temperatures above 400° C., or required a catalyst to trigger cross-linking, which catalyst was therefore trapped in the resulting thermoset structure. Trapping of catalyst in the product thermoset part is undesirable because most catalysts also catalyze oxidative degradation and therefore reduce the lifetime at high temperatures. Catalysts are also detrimental in electronics applications where even trace metals can affect performance.

It would be desirable to provide a polyquinoline composition which could be cured without the use of a catalyst. It would also be desirable to provide polyquinoline compositions which have large processing windows; that is, at least a 50° C. difference between the $T_g$ (or $T_m$, where appropriate) and the curing temperature. If the curing temperature is lower than the $T_g$ (or $T_m$), the polymer will not flow before curing and, therefore, will not consolidate well.

SUMMARY OF THE INVENTION

The present invention provides polymers which comprise quinoline repeat units and end groups comprising an acetylene functionality as well as cross-linked compositions formed therefrom.

In one embodiment, the polymers have the formula:

where PQ is a polyquinoline polymer repeat unit, n is 1 to 100,000, E" is an end group selected from —C≡CR, —Ar C≡CR, —CH$_2$C≡CR, —Ar—OCH$_2$C≡CR, and —OCH$_2$C≡CR, R is H, alkyl, aryl or heteroaryl, Ar is arylene or heteroarylene, where Ar may be optionally substituted with alkyl, aryl, alkoxy, aryloxy, chloro, fluoro, fluoroalkyl, fluoroaryl, and nitro, and R may be optionally substituted with alkoxy, aryloxy, chloro, fluoro, fluoroalkyl, fluoroaryl, and nitro.

The thermosetting polyquinolines of the present invention have many applications, including being cast into freestanding films or coated onto substrates. After the casting or coating process, the polymers are heated and cured to a desired extent, thereby resulting in a thermoset polymer capable of withstanding high heat and degradation by solvents.

BRIEF DESCRIPTION OF THE DRAWINGS

These and other features, aspects and advantages of the present invention will be more fully understood when considered with respect to the following detailed description, appendant claims, and accompanying drawings wherein:

FIG. 2 is a DSC trace for the propargyl endcapped polymer prepared in accordance with Example 5.

DETAILED DESCRIPTION

Figure 1:
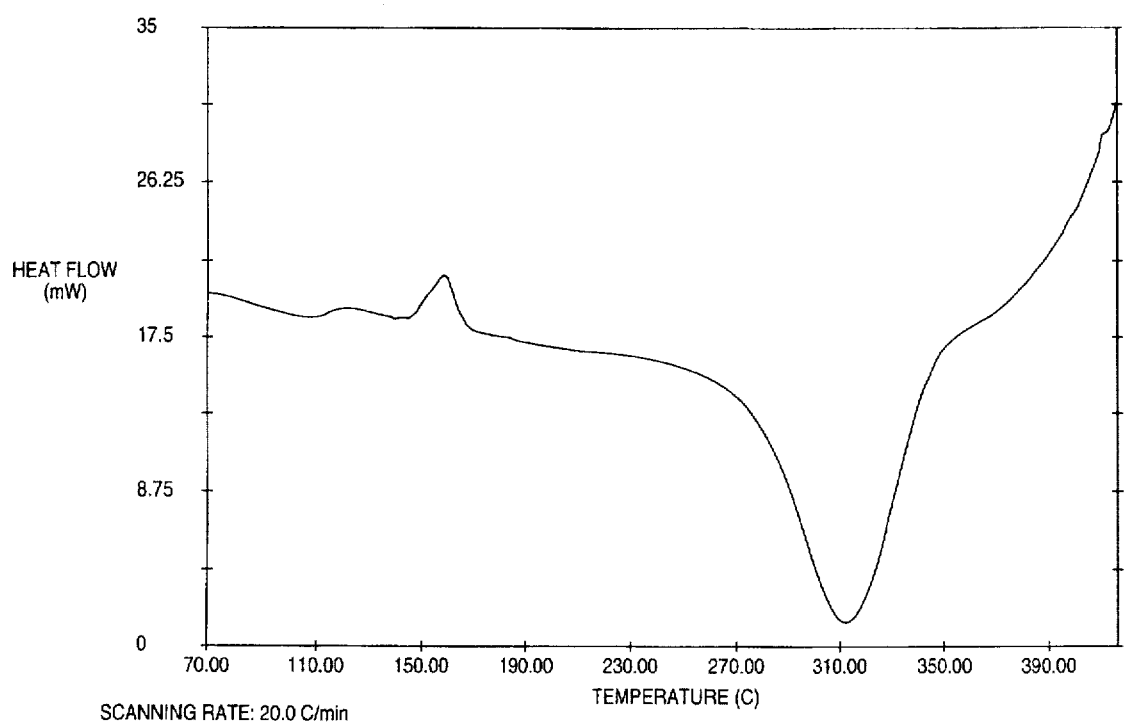
FIG. 1 is a DSC trace for the propargyl endcapped polymer prepared in accordance with Example 7.

In accordance with practice of the present invention, a polyquinoline polymer having reactive end groups which cross-link on heating is provided. The reactive end groups contain the acetylene function which is further substituted to control reactivity and, therefore, the cross-linking temperature.

The general formula for the thermosetting polyquinolines of the present invention is:

E"—(PQ)$_n$—E"

where PQ is a polyquinoline polymer repeat unit, n is the average number of repeat units, E" is an end group selected from —C≡CR, —Ar—C≡CR, —CH$_2$C≡CR, —Ar—OCH$_2$C≡CR, and —OCH$_2$C≡CR, where R is H, alkyl, aryl or heteroaryl, and Ar is arylene or heteroarylene. Ar may be optionally substituted with alkyl, aryl, alkoxy, aryloxy, chloro, fluoro, fluoroalkyl, fluoroaryl, and nitro. R may be optionally substituted with alkoxy, aryloxy, chloro, fluoro, fluoroalkyl, fluoroaryl and nitro.

Non-limiting examples of alkyl are methyl, ethyl, propyl, isopropyl, benzyl, and hexyl.

Non-limiting examples of aryl are phenyl, 3-methoxyphenyl, 4-chlorophenyl, naphthyl, tolyl, and biphenyl.

Non-limiting examples of heteroaryl are 2-pyridyl, 4-pyridyl, 2-quinoline, and 2-benzoxazole.

Non-limiting examples of arylene are 1,4-phenylene, 1,3-phenylene, 2-methyl-1,4-phenylene, 1,4-naphthylene, and 4,4'-biphenylene.

Non-limiting examples of heteroarylene are 2,4-pyridinediyl, 2,4-quinolinediyl, 2,6-quinolinediyl, 4-phenyl-2,6-quinolinediyl, and 3,6-quinolinediyl.

Non-limiting examples of —C≡CR are —C≡CH (ethynyl), —C≡C—C$_6$H$_5$ (phenylethynyl), —C≡C—C$_6$H$_4$O C$_6$H$_5$ (phenoxyphenylethynyl), and —C≡CCH$_3$.

Non-limiting examples of —Ar—C≡CR are —C$_6$H$_4$—C≡CH, and the three structures shown below:

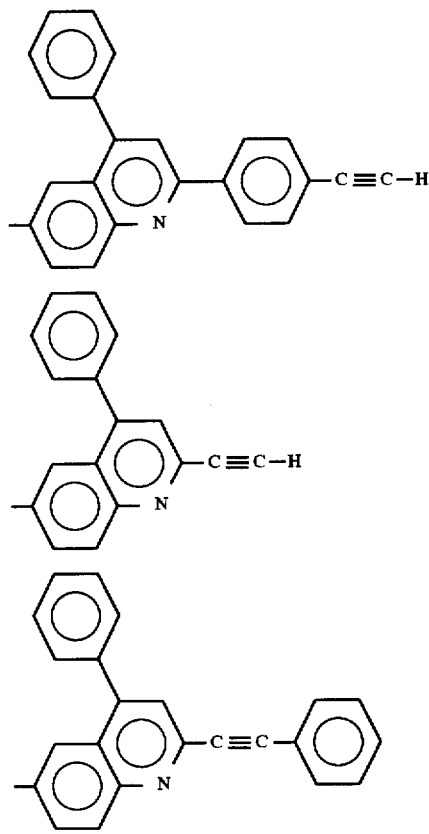

Non-limiting examples of —OCH$_2$C≡CR (propargyl ether) are —OCH$_2$C≡CH and —OCH$_2$C≡CCH$_3$.

Non-limiting examples of —Ar—OCH$_2$C≡CR are —C$_6$H$_4$—OCH$_2$C≡CH, —C$_6$H$_4$—OCH$_2$C≡CCH$_3$, and —C$_6$H$_4$—OCH$_2$C≡CC$_6$H$_5$.

Non-limiting examples of —CH$_2$C≡CR (propargyl) are —CH$_2$—C≡CH and —CH$_2$C≡C$_5$H$_6$.

The naming of the end groups is dependent on the synthetic method and may have more than one possible alternative. The preferred functional name, e.g., propargyl, may not coincide with the actual end group; for example, if the monomers are F—AA—F and H—BB—H, where H—BB—H is a diol in slight excess, and the polymerization reaction is:

F—AA—F+H—BB—H+K$_2$CO$_3$→H—BB—(AA—BB)$_x$—H+KF+ CO$_2$+H$_2$O

Technically, the end group is H—, although the functional end group is —OH, since H—BB—H is a diol (e.g., HO—C$_6$H$_4$—OH). If essentially the same polymer was prepared by using a monomer offset in the other direction (F—AA—F in slight excess), followed by hydrolysis of the fluorine end groups, the end groups would be both technically and functionally —OH; for example,

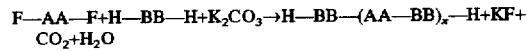

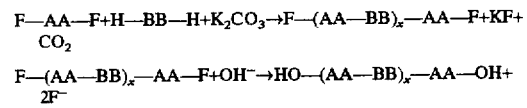

Similarly, in some instances, an end group might be considered to be either a propargyl group or a propargyl ether group. It is assumed that one skilled in the art will understand the meaning of a particular end group name from the context in which it is used.

Preparation of Polyquinoline Polymers

As is described in the "Background of the Invention" section, polyquinoline polymers have been prepared by the Friedlander condensation as disclosed in the '187 patent, or can be prepared by nucleophilic displacement polymerization as disclosed in the '993 application. Either of these methods or others known in the art may be used to provide the polymers of the present invention. The polymers of the present invention contain specific end groups which can be incorporated either during the polymerization reaction by addition of specific endcappers, or by modification of the polymer end groups in a post-polymerization reaction.

As is described in the '187 patent, polyquinoline polymers can be prepared from the reaction of (a) an aromatic amino carbonyl containing two sets of ortho-amino carbonyl functions attached to an aromatic nucleus (defined herein as a type AA monomer), selected from the group of compounds consisting of the structures represented by the formulas:

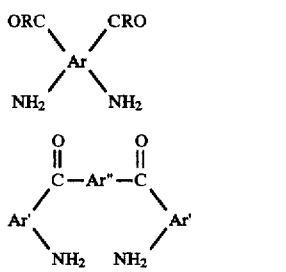

wherein R is hydrogen or aryl, and the Ar, Ar', and Ar" are arylene groups, with (b) a bis-methylene ketone (ketomethylene) compound (defined herein as a type BB monomer), selected from the group of compounds consisting of the structures represented by the formulas:

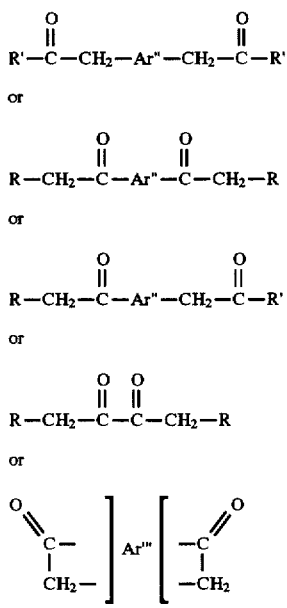

wherein R is hydrogen or aryl, R' is aryl, Ar" is an arylene group, and Ar''' is an arylene group, four positions of which are occupied by connection of the methylene carbonyl functions.

Subsequently, it has been reported in the literature (J. K. Stille, *Macromolecules*, 1981, 14, 870–880) that related polyquinoline polymers can be prepared from the reaction of a compound containing one set of ortho-amino carbonyl functions, as well as one methylene ketone function attached to an aromatic nucleus (defined herein as a type AB monomer), selected from the group of type AB compounds consisting of structures represented by the formulas:

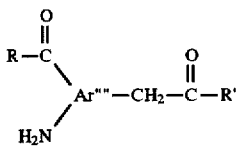

(8)

or

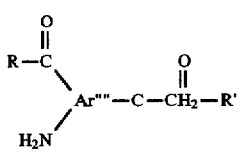

(9)

or

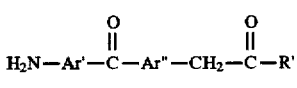

(10)

or

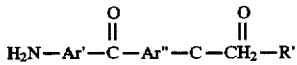

(11)

wherein R is hydrogen or aryl, R' is aryl, and Ar', Ar", and Ar'''' are arylene groups. (The Stille article is incorporated herein by reference.)

The polyquinoline polymers are produced by reacting the AA monomer with the BB monomer by allowing equimolar amounts or nearly equimolar amounts of the two to react in the presence of either an acid or a base catalyst in a suitable solvent. An inert atmosphere for the reaction is preferable, although not necessary. The reaction takes place at room temperature or below, but convenient reaction temperatures are from about 25° C. to 250° C., and usually about 25° C. to 200° C. To expedite the reaction, the temperature is raised gradually throughout the course of the reaction until temperatures of about 190° C. are reached. The acid catalysts can be either protonic or Lewis acids. Hydrogen halides (fluoride, chloride, bromide or iodide), sulfuric acid, a sulfonic acid, e.g., as toluenesulfonic acid, phosphoric acid, polyphosphoric acid, trifluoroacetic acid, and the like, are examples of protonic acid catalysts, while boron fluoride, phosphorous pentafluoride, aluminum chloride, antimony trifluoride, antimony pentafluoride, antimony trichloride, stannic chloride, and the like, are examples of Lewis acid catalysts. The base catalysts can be either hydroxylic or Lewis bases. Sodium hydroxide, potassium hydroxide, calcium hydroxide, lithium hydroxide, and the like, are examples of hydroxylic base catalysts, while N-ethyl morpholine, triethyl amine, 1,5-diazabicyclo[4.3.0]non-5-ene, 1,4-diazabicyclo[2.2.2] octane, and the like, are examples of Lewis base catalysts.

A wide variety of solvents are available for either the acid or the base catalyzed reaction. The solvent employed for these reactions should not react under the reaction conditions with either the acid or the base catalyst or with any of the functional groups on the monomers, such that this reaction would have an adverse effect on the polymerization reaction. Benzene, chlorobenzene, 1-chloronaphthalene, tetralin, acetic acid, formic acid, phenols, e.g., m-cresol, o-, m-, and p-dichlorobenzene (or mixtures thereof), polyphosphoric acid, and the like, are solvents which can be used in the acid catalyzed reactions. Dimethylsulfoxide, hexamethylphosphorictriamide, dimethylformaide, tetrahydrothiophene dioxide, dimethylacetamide, N-methylpyrrolidone, and the like, are solvents which can be used in the base catalyzed reaction.

The aromatic amino carbonyl monomers suitable for processes disclosed in the '187 patent can be prepared in a variety of ways well known in the art but are often prepared by combinations of organic reactions, including acylations, oxidations, and reductions. The synthesis of 4,6-diaminoisophthalaldehyde is described in Ruggli et al., *Helv. Chim. Acta.*, 20, 272 (1937), of 2,5-diaminoterephthalaldehyde in Ruggli et al., *Helv. Chim. Acta*, 27, 274 (1944), of 4,6-dibenzoyl-m-phenylenediamine in Chardonnes et al., *Helv. Chim. Acta*, 38, 393 (1955), of 2,5-dibenzoyl-p-phenylenediamine in Kinsey et al., *J. Chem. Soc.*, 1 (1958), and of 2,2'-diaminoisophthalophenone in Simpson et al, *J. Chem. Soc.*, 646 (1945).

The methylene ketones suitable for processes disclosed in the '187 patent can be prepared in a variety of ways well known in the art but are often conveniently prepared by Friedel-Crafts reactions of acid chlorides on aromatic nuclei. The synthesis of 1,4-diphenylacylbenzene is described in Schilling et al., *Macromolecules*, 2, 85 (1969), of 1,4-diphenacetylbenzene in Ogliaruso et al., *J. Org. Chem.*, 30 3554 (1965), of 4,4'-diphenacetylphenyl ether, 4,4'-diphenylacetylphenyl sulfide and 4,4'-diphenacetylbiphenyl in Ogliaruso et al., *J. Org. Chem.*, 28, 2725 (1963), of p-diacetylbenzene in Berend et al., *J. Prakt. Chem.*, 74, 134 (1906), of 1,3-diacetylbenzene in J. Bowman, *J. Chem. Soc.*, 323 (1950), of 4–4'-diacetylphenyl ether in H. Kipper, *Chem. Ber.*, 38, 2491 (1905), of 2,6-diacetylpyridine in Terent'ev et al., *Zh. Vses. Khim. Obshch. im. D.I. Mendeleeva*, 6, 116 (1961), of 4,4'-diacetyldiphenylsulfide in C. M. Smith, U.S. Pat. No. 2,903,461 (1959), of 4,4'-diacetyldihenylsulfone in P. Hu., *J. Chem. Soc.*, 178 (1959), of 4,4'-diacetylbiphenyl in Tani et al., *Bull. Chem. Soc. Jap.*, 36, 391 (1963), of dibenzo[a,e]-cyclooctene-5,11 (6H,12H) dione in Yates et al., *Can. J. Chem.*, 48, 788 (1970), and of 1,10-diketo[2.2]metacyclophane in Hylton et al., *J. Amer. Chem. Soc.*, 90, 6887 (1968).

The complete disclosures of the above articles relating to the methods for preparation of the amino carbonyl compounds and the methylene ketones are incorporated herein by reference and also represent the types of syntheses employed for the preparation of such compounds.

In the nucleophilic displacement reaction described in the '993 application, the type AA monomer comprises two fluoro groups, where each such fluoro group is activated by a quinoline nucleus. The type BB monomer is a diol which may be any diol stable to the basic conditions of the reaction. The difluoro (type AA) monomer is reacted with the diol (type BB) monomer in the presence of a base in a dipolar solvent to thereby form the polyquinoline polymer. The type AB monomers are fluorohydroxy monomers which comprise a quinoline nucleus containing a single activated fluoro group and a single hydroxy group. The AB monomers are reacted in the presence of a base in a dipolar solvent.

There are two types of difluoro (type AA) monomers useful in accordance with the '993 disclosure, i.e., those which contain a single quinoline nucleus and those which contain two quinoline nuclei connected directly through a linking group. The general structure of the difluoro (AA) monomers which contain a single quinoline nucleus is given by the following structural formula:

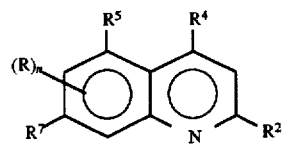

wherein $R^2$, $R^4$, $R^5$, and $R^7$ are selected from the group consisting of any groups which do not interfere with the polymerization reaction, including but not limited to alkyl, aryl, aryloxy, alkoxy, ketone, formyl (—COH), ester (—CO$_2$R" or —OCOR"), amide (—NR"COR'" or —CONR"R'"), heteroaryl, cyano, (where two adjacent R groups may be bridging groups (non-limiting examples of R bridging groups being —(CH$_2$)$_4$—, —(CH$_2$)$_3$—, and —CH=CH—CH=CH—)), and F or ZF, wherein exactly two of $R^2$, $R^4$, $R^5$, $R^7$ are F or ZF, wherein Z is selected from the group nil, ortho-arylene, and para-arylene, and (R)$_n$ are any independently selected R groups, such as the $R^2$, $R^4$, $R^5$, $R^7$ groups listed above, which do not interfere with the polymerization reaction. The (R)$_n$ group(s) may be at one or more of the 3, 6 or 8 positions on the quinoline nucleus. The R" and R'" groups are alkyl or aryl.

Non-limiting examples of ortho-arylene are 1,2-phenylene, 1,2-naphthylenediyl, 2,3-naphthylenediyl, 1,2-(4-phenylphenylene), 1,2-(4-methoxyphenylene), and 1,2-(3-methylphenylene). Non-limiting examples of para-arylene are 1,4-phenylene, 1,4-naphthylenediyl, 1,4-(2-phenylphenylene), 1,4-(2-methoxyphenylene), and 1,4-(2,5-dimethylphenylene).

The general structure of the difluoro (AA) monomers useful in accordance with the '993 disclosure which contain two quinoline nuclei is given by the following structural formula:

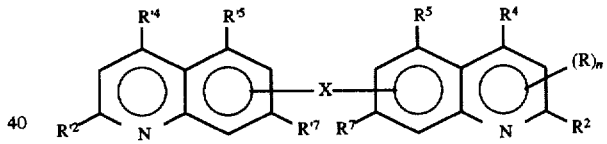

where $R^2$, $R^4$, $R'^2$, and $R'^4$ may be chosen independently from F and Z—F (where Z, as defined above is nil, ortho-arylene, and para-arylene); $R^5$, $R^7$, $R'^5$, and $R'^7$ may be F, and exactly one of $R^2$, $R^4$, $R^5$, and $R^7$ is F or Z—F and exactly one of $R'^2$, $R'^4$, $R'^5$, and $R'^7$ is F or Z—F, and the remaining positions on the quinoline nuclei (the 3, 6, 8, 3', 6', and 8' positions) are occupied by H or R, where (R)$_n$ are any independently selected R groups, with R being any group that does not interfere with the polymerization reaction including but not limited to alkyl, aryl, alkoxy, aryloxy, ketone, formyl (—COH), ester (—CO$_2$R" or —OCOR"), amide (—NR"COR'" or CONR"R'"), heteroaryl, cyano and where two adjacent R groups may be bridging groups, non-limiting examples of such R bridging groups being —(CH$_2$)$_4$—, —(CH$_2$)$_3$—, and —CH=CH—CH=CH—. The R" and R'" groups are alkyl or aryl. The divalent linking group X links the two quinoline nuclei and may be attached at any position on either ring. The X groups can be any divalent group which does not interfere with the polymerization reaction; e.g., X should not contain strong nucleophiles like oxy anions, or good leaving groups like activated halides. The divalent linking group X may be chosen from:

nil,

—O—,

—S—,

—C(O)—,
—S(O)—,
—S (O$_2$)—,
—W—,
—(—O—W—)$_m$—O—, m=1–3, and
—Q—;

where W is a divalent group selected from the group consisting of:

—Ar'—(where Ar' means arylene),
—Het—(where Het means heteroarylene),
—Ar'—O—Ar'—,
—Ar'—C (O)—Ar'—,
—Ar'—S—Ar'—,
—Ar'—S(O)—Ar'—,
—Ar'—S (O)$_2$—Ar'—, and
—Ar'—Q—Ar'—;

and where Q is a divalent group containing a quaternary carbon as shown below:

Q= 

U, U'=—CH$_3$, —CF$_3$, Ar, or bridging where if U and U' are bridging, they may be alkyl, aryl, alkaryl, ether, ester, amide, alkyl ketone, aryl ketone, and may be partially or fully substituted with fluorine. Non-limiting examples of bridging U,U' groups are:

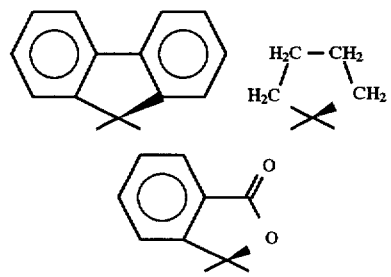

The type AA monomers may be prepared by coupling pre-formed chlorofluoroquinolines or, alternatively, bis-aminobenzene derivatives may be condensed into bis-quinolines using the Friedlander or other quinoline-forming condensations known in the art.

Non-limiting examples of fluorohydroxy (AB) monomers useful in accordance with the process disclosed in the '993 application include: 2-(4-fluorophenyl)-6-hydroxy-4-phenylquinoline, 2-(2-fluorophenyl)-6-hydroxy-4-phenylquinoline, 4-(2-fluorophenyl)-6-hydroxy-2-phenylquinoline, 2,3-diphenyl-4-(2-fluorophenyl)-6-hydroxyquinoline, 2,3-diphenyl-4-(4-fluorophenyl)-6-hydroxyquinoline, 2,3-diphenyl-6-(2-fluorophenyl)-4-hydroxyquinoline, 2,3-diphenyl-6-(4-fluorophenyl)-4-hydroxyquinoline, 7-fluoro-2-hydroxyquinoline, 7-fluoro-2-hydroxy-4-phenylquinoline, 7-(4-fluorophenyl)-2-hydroxy-4-phenylquinoline, 7-fluoro-4-hydroxy-2-phenylquinoline, 7-(4-fluorophenyl)-4-hydroxy-2-phenylquinoline, 2-(4-fluorophenyl)-3-hydroxyquinoline, 2,-(4-fluorophenyl)-4-hydroxy-3-phenylquinoline, 2-(4-fluorophenyl)-6-hydroxy-3-phenylquinoline, 2-(4-fluorophenyl)-8-hydroxy-3-phenylquinoline, 2-(4-fluorphenyl)-8-hydroxyquinoline, and 2-(2-fluorophenyl)-4-(4-hydroxyphenyl)quinoline.

The type AB monomers may be prepared using any of the various methods for quinoline synthesis known in the art,
including Friedlander synthesis, Skruap synthesis, Doebner synthesis, Niementowski synthesis, and the like. These quinoline-forming reactions are listed, for example, in The Merck Index, Tenth Edition, M. Windholz, Ed., Merck & Co., Rahway, N.J. 1983, which is incorporated herein by this reference. For example, the commercially available 2-amino-4-fluorobenzoic acid can be converted into 7-fluoro-4-hydroxyquinolines substituted at the 2 position with various groups derived from co-reactant α-methylene ketone derivatives by using the Niementowski synthesis. Various α-methylene ketone derivatives are described in the '187 patent. 3-aminophenol may be converted into hydroxyquinolines substituted at the 2 and/or 4 positions by condensations with acrolein derivatives (e.g., 4-fluorocinnamaldehyde) via the Doebner-Miller synthesis. Similarly, 2-aminophenol and 4-aminophenol may be condensed to give fluorohydroxyquinolines.

Diol (BB) monomers useful in accordance with the disclosure of the '993 application are of the structure H—Y—H, where Y is selected from —O— and —O—W—O— and W is as defined above.

Non-limiting examples of diol monomers useful as monomers are bis-phenol AF

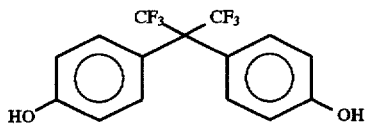

and 9,9-bis-(4-hydroxyphenyl)fluorene

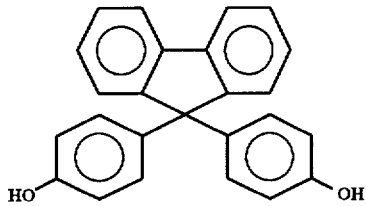

The diol monomers are present as a bis-oxide salt (e.g. dipotassium isopropylidene-bis-phenolate, and the like) or the reaction for preparing the polyquinolines disclosed in the '993 application is carried out in the presence of a base capable of deprotonating the diol. Such bases include alkali and alkali earth metal carbonates and hydroxides, such as potassium carbonate, potassium hydroxide, sodium carbonate, sodium hydroxide, and the like. Stronger bases such as sodium hydride or other metal hydrides, butyl lithium, sodamide or other metal amides, and the like may be used if the diol is not acidic enough to be sufficiently deprotonated by sodium hydroxide.

The polymers disclosed in the '993 application result from nucleophilic displacement by an oxy anion of fluoride activated by a quinoline nucleus. These types of displacement reactions are best performed in an anhydrous dipolar solvent, non-limiting examples of which include N,N-dimethylformamide (DMF), N,N-dimethylacetamide (DMAC), N-methylpyrrolidinone (NMP), tetramethylurea, dimethylsulfoxide, sulfolane, and diphenylsulfone, or mixtures of these solvents with other anhydrous solvents. The addition of toluene, dichlorobenzene, or other solvent which forms an azeotrope with water may be desirable in order to azeotropically distill off water. In one embodiment, the diol monomer is allowed to react with potassium carbonate or other base to form the potassium salt, and by-product water. This water is easily removed by azeotropic distillation (see examples). Isolation of the salt form of the diol monomer is not necessary; it may be formed and used in situ.

The general procedure outlined in the '993 application for preparing polyquinoline polymers comprises heating the monomer(s) and a base in an anhydrous solvent and azeotropically removing water (formed by the reaction of the base with the hydroxy groups on the BB or AB monomer). Alternatively, the BB or AB monomer(s) may be treated with base in a separate step and the corresponding oxide salt (bis-oxide salt for a BB monomer and oxide salt for AB monomer) isolated and purified as necessary. The order of addition of the reactants is not important. The amounts of the monomers used to from the polymers of the present invention may be determined by standard formulae known in the art, such as Carother's equation.

In general, (for AA+BB polymerization) while equal molar amounts of AA and BB monomers are normally used, molar ratios other than 1:1 may be used, if desired, to control the MW or end groups. Base is generally added in slight molar excess. For the solvent system NMP/toluene the reflux temperature is about 135° C., and water is collected over a six- to eighteen-hour period. The toluene or other co-solvent is then removed by distillation and the mixture brought to reflux (about 202° C. for NMP) and held for 12 to 24 hours, or until the desired polymer MW is achieved. Pressure is not critical; atmospheric pressure is preferred.

Endcappers, if desired, may be added at the beginning of the reaction, during the reaction, or near the end of the reaction. Such endcappers may be used to control the MW of the product polyquinoline, and, typically, a portion of the endcapper moiety will remain as an end group E. The polymer MW may be determined as is known in the art by measurement of viscosity or by gel permeation chromatography (size exclusion chromatography). The reaction is then cooled. The polymer may be recovered from the dope by any technique known in the art, including by precipitation with a non-solvent such as alcohol or water. The non-solvent is preferably chosen to be polar in order to remove fluoride salts which are the by-product of the reaction. It is also preferable to filter the polymer dope before precipitation. In some cases, it may be desirable to dilute the dope before filtration or precipitation.

In one embodiment of the procedure outlined in the '993 application, the general structures of the type AB monomers is given by:

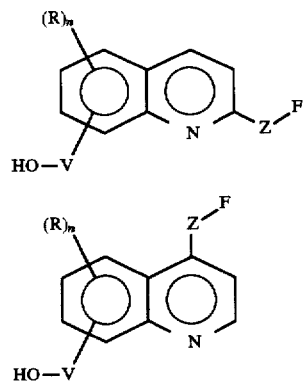

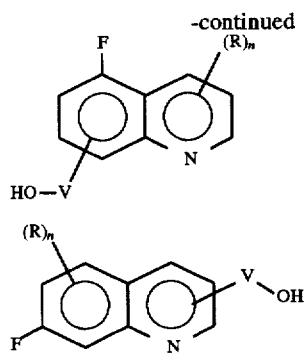

where Z is chosen from nil, ortho-arylene, and para-arylene, the V—OH group may be at any position of the quinoline nucleus including either ring, the group V may be chosen as any divalent group that does not interfere with the polymerization reaction, including but not limited to nil, alkyl, arylene, mixed alkyl/arylene, alkoxy, aryloxy, alkyl ketones aryl ketone, alkyl sulfone, aryl sulfone, alkyl thioether, aryl thioether, and heteroarylene, and n is 0 to 5 and $(R)_n$ are any groups not interfering with the polymerization reaction including but not limited to alkyl, aryl, aryloxy, ketone, formyl, ester, amide, heteroaryl, cyano and bridging groups.

Non-limiting examples of divalent V groups are as follows:

alkyl groups are methyl, ethyl, and stearyl;
arylene groups are phenylene and naphthylenediyl;
mixed alkyl/arylene groups are dimethylphenylene and ethylenephenylene ($-CH_2CH_2-CH_6H_4-$);
alkoxy groups are methyleneoxy and propyleneoxy;
aryloxy groups are naphthaleneoxy and phenyleneoxy;
alkyl ketone groups are acetyl and cyclohexylcarbonyl;
aryl ketone groups are methylphenylenecarbonyl and phenylenecarbonyl;
alkyl sulfone groups are methylene sulfone and ethanesulfone;
aryl sulfone groups are naphthalene sulfone and phenylene sulfone;
alkyl thioether groups are ethylenethio ($-CH_2CH_2-S-$) and propylenethio;
aryl thioether groups are biphenylenethio and phenylenethio ($-C_6H_4-S-$); and
heteroarylene groups are pyridinediyl and quinolinediyl.

The $(R)_n$ may be at any position of the quinoline nucleus not occupied by Z or V—OH, including either ring.

The AB monomers of the above described general structures may be polymerized to give polymers of the corresponding structures shown below:

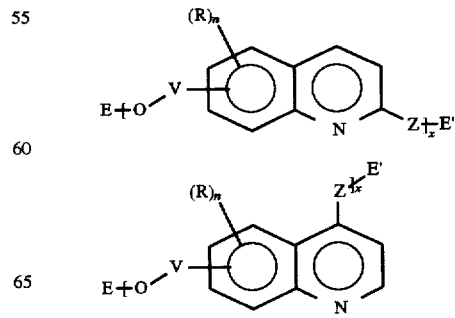

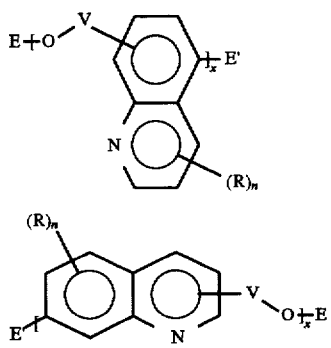

where E and E' are end groups and x is the number of repeat units. The number of repeat units x is preferably 2 to 1,000,000, more preferably 10 to 10,000, and most preferably 50 to 1000. If no endcappers are added, E is H and E' is F, except that adventitious endcappers derived from impurities and side reactions may also be present. Where E is H the chemical functional group at the polymer end is hydroxy. The reactivity of this end group is that of a hydroxy group. When speaking of the chemical nature of the end group it may be more appropriate to refer to E as hydroxy or OH, even though E is shown as H. In the cases of the present invention, the most likely adventitious E' is —OH derived from water. Endcappers may be added intentionally; for example, phenol will yield a phenoxy endcap (E'=Oph), and 2-fluoroquinoline will yield a quinoline endcap (E=2-quinolyl).

The end groups can significantly alter the chemistry and reactivity of the product polymer. For example, fluoride end groups will be subject to nucleophilic attack, and can be further substituted by other nucleophiles. For example, the fluoride end group could be displaced by dyes or other labeled groups. A polymer having fluoride end groups could be reacted with a diol (possibly different than the original BB monomer diol) to form a new polymer of higher MW and possibly of a more complex structure. A polymer having fluoride end groups could be reacted with a trifunctional nucleophile, such as a triol, or a triamine, to form a branched or cross-linked polymer.

As in the case with fluoride end groups, hydroxy end groups are also reactive. Hydroxy end groups are acidic and when deprotonated by base are nucleophilic. These characteristics may be used in further reactions on the polymer, for example, to form esters or ethers. A hydroxy terminated polymer will react, for example, with a diacid chloride to form a polyester. Non-limiting diacid chlorides are adipoyl chloride, terephthaloyl chloride, succinoyl chloride, and the like. Hydroxy end groups may also be used to cross-link or form branched structures.

Exemplary polymers derived from the polymerization of AB monomers are shown below:

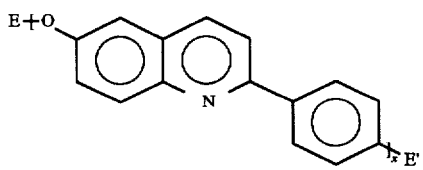

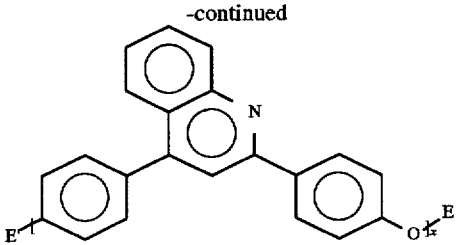

where E and E' are end groups as described above and x is the number of repeat units.

In an exemplary embodiment of the process disclosed in the '993 application, single quinoline nucleus difluoro (AA) monomers may be allowed to react with diol (BB) monomers as is described below to form polymers having the general structure:

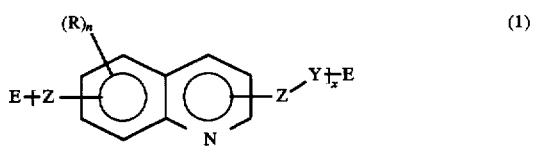

(1)

where $(R)_n$ and Z are as described above, and x is the number of repeat units, and the Z groups are attached to the quinoline nucleus at positions chosen from 2,4,5 and 7, and if a —Z—Y— group is attached to positions 5 or 7, then Z=nil, i.e., only Y is present, Y is a divalent moiety chosen from —O— and —O—W—O—, where W is defined above, and E are end groups, the structures of which depend on the relative amounts of AA and BB monomers present and on added endcappers. For example, if there is an excess of AA monomers, the end groups can be A, and if there is an excess of BB monomers, the end groups can be B.

In accordance with one embodiment of the process of the '993 application, the reaction of a difluoro (AA) single quinoline monomer with a diol monomer to produce a polyquinoline polymer under the general reaction conditions outlined above is exemplified by:

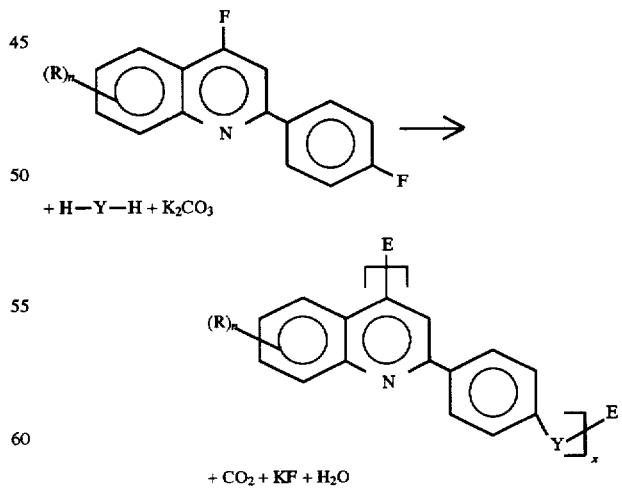

The double quinoline nuclei difluoro (AA) monomers may be used as described below to form polymers having ten general structures, the first three of which are shown below as structures (2), (3), and (4):

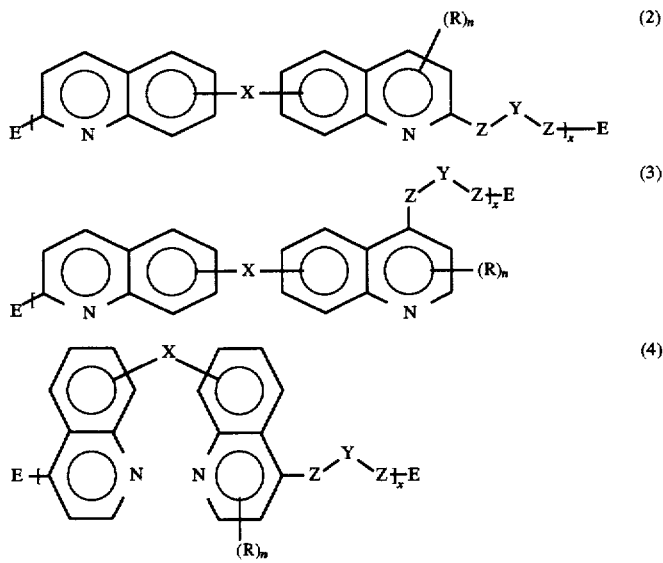

The seven additional general structures have the quinoline nuclei attached to the polymer chain through positions 2 and 5', 2 and 7', 4 and 5', 4 and 7', 5 and 5', 5 and 7', and 7 and 7'.

An exemplary embodiment of a more particular General Structure (2)-type Polyquinoline is given by the following structure:

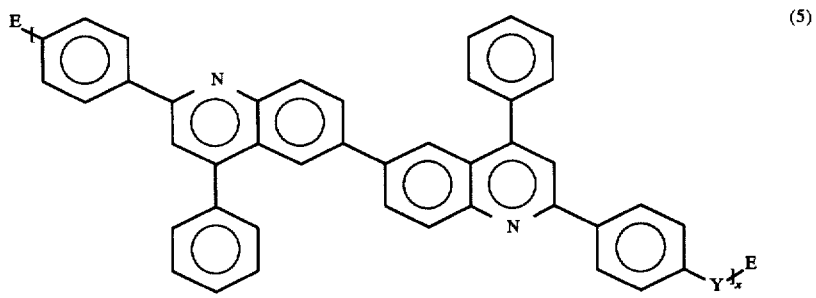

In the polymer of the structure 5, both Z's have been chosen a para-phenylene, $R^4$ and $R'^4$ have been chosen as R groups equal to phenyl, and all other R's are H.

A specific example of Structure 5 would be:

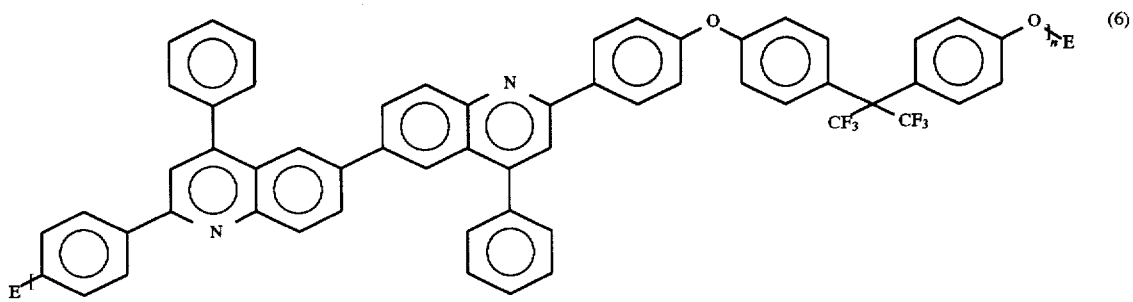

where the structure 6 polymer is formed by reacting the appropriate difluoro AA monomer with his-phenol AF, so that Y is bis-phenoxyhexa-fluoroisopropylidene, and X is nil. In structure 6, the end groups E are F and OH, as would occur if the two monomers were used in equal amounts; n is the number of repeat units.

Preparation of Thermosetting Polyquinolines

In a first embodiment of preparing thermosetting polyquinolines of the present invention, an endcapper incorporating an acetylene group is added to the polymerization reaction in a Friedlander condensation or in a nucleophilic displacement polymerization. Both Friedlander and nucleophilic polymerizations are types of "step-growth" polymerization. Such step-growth-type polymerization is well known, and one skilled in the art will know how to calculate the amount of monomers and endcappers to add to achieve a particular molecular weight. Methods of calculating monomer amounts are described for example in G. Odian, *Principles of Polymerization*, Third Edition, 1991, John Wiley &

Sons, Inc., New York, which is incorporated herein by reference. Odian discusses molecular weight control in Chapters 2–6.

As an example, consider a polymerization requiring two monomers, AA and BB, where A and B represent complementary functional groups which can react to form polymer linkages. As is described above, these monomers will react to form growing chains that may have either A or B type ends, e.g. AA—BB—AA—BB—AA (A type ends) or AA—BB—AA—BB (one end A type, one end B type), or BB—AA—BB—AA—BB (B type ends). If an endcapper AE" (an endcapper with an acetylene functionality) is added, where E" is inert to the reaction conditions, chain ends that react with AE" will stop growing. In the simplest case, one extra molar equivalent of BB should be added for each two molar equivalents of AE" endcappers added. The identification of the endcappers as an AE" endcapper is for illustration. It should be understood that BE" endcappers could also be used.

Assuming 100% yield at each step, the MW of the polymer may then be determined by:

number of repeat units=$DP_n$=2x (moles of AA+moles of BB)/(moles of AE") where the repeat units are —AA— or —BB—, and $DP_n$ is the number average degree of polymerization. If 100 moles of AA monomer, 102 moles of BB monomer, and 4 moles of AE" endcapper are used the $DP_n$ will be 2x (100+102)/4=101.

It may be desirable to perform several control experiments to determine the relative reactivity of monomer and endcapper, and to determine the monomer offset if two or more monomers are required. For example, a set of polymerizations in which the ideal AA/BB molar ratio as calculated above is changed by +0.25%, +0.5%, –0.25% and –0.5% may be run and the resulting MWs compared to the ideal case. The monomer offset that gives the MW closest to the desired MW should be used. If the change to the AA/BB molar ratio shows a trend in the direction of the desired MW, but the change was not sufficient to reach the desired weight, further experiments can be run to fine tune the change in the AA/BB molar ratio to determine the exact ratio which will provide a polymer of the desired weight.

As is well known in the art, these control experiments will allow one to correct for adventitious impurities and side reactions which may alter the actual MW from that calculated for the ideal case, as above.

Non-limiting examples of AE" (or BE") endcappers, where E" is as defined above, are:

Friedlander

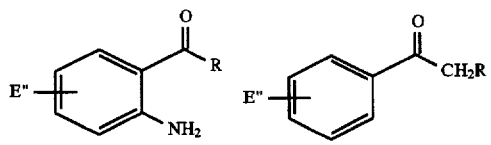

where R is as defined above for the Friedlander polymerization as H or aryl.

Nucleophilic Displacement

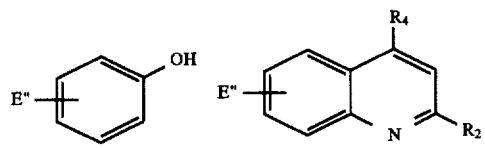

where $R_2$ and $R_4$ are independently selected from H, phenyl, fluoro, 2-fluorophenyl, or 4-fluorophenyl, and wherein only one of the $R_2$ and $R_4$ groups are fluoro, 2-fluorophenyl, or 4-fluorophenyl.

The endcappers AE" or BE" may also contain fused rings, as for example:

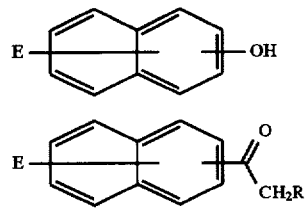

where R is hydrogen or aryl.

Specific non-limiting examples of endcappers for use in Friedlander polymerizations include the 3-, 4-, 5-, and 6-(2-phenylethynyl) isomers of 2-aminobenzophenone, and the 2-, 3-, and 4-(2-phenylethynyl) isomers of acetophenone.

Specific non-limiting examples of endcappers for use in nucleophilic displacement polymerizations include the 2-, 3-, and 4-hydroxy isomers of diphenyl acetylene, the 2-and 3-(2-phenylethynyl) isomers of 4-fluorobenzaldehyde and 2-(4-fluorophenyl)-4-phenyl-6-phenylethynylquinoline.

Each of the above-listed AE" endcapper monomers can be prepared through a cuprous iodide catalyzed coupling reaction between phenyl acetylene and the appropriate brominated derivatives. For example, 3-(2-phenylethynyl)-4-fluorobenzaldehyde can be prepared from the reaction between phenyl acetylene and 3-bromo-4-fluorobenzaldehyde. The reactive groups, i.e., hydroxides or amines, in some of these examples may first have to be protected with standard protecting groups before coupling and then deprotected before use.

In a second embodiment of the present invention a polyquinoline is prepared having end groups that may be later transformed into the desired acetylenic end groups. For example, a hydroxy terminated polyquinoline, HO—(PQ)$_n$—OH may be prepared by nucleophilic displacement polymerization and subsequently treated with propargyl bromide to form a propargyl ether terminated polyquinoline:

where n=the number of polyquinoline repeat units.

In another embodiment of the present invention, a fluoro terminated polyquinoline prepared by nucleophilic displacement may be treated with an acetylene salt to form polymers having end groups with acetylene functionality:

The hydroxy and fluoro terminated polyquinolines generally described above can be prepared by nucleophilic displacement polymerization using a monomer offset to control end groups (see examples below). The MW may be controlled by monomer offset as above, using methods well known in the art.

19

As is described above, the Friedlander polymerization method can be used to prepare polyquinolines terminated either with a methylene ketone (B) end group or an ortho amino carbonyl (A) end group, or a combination of one methylene ketone end group and one ortho amino carbonyl end group.

The methylene ketone end groups may be converted into acetylene groups to provide the polymers of the present invention by known methods; for example,

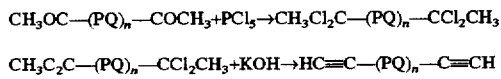

The ortho amino carbonyl end groups may be converted into acetylene groups, for example, by reaction with 4-phenylethynylacetophenone. The preparation of 4-phenylethynylacetophenone is set forth in Example 9 below:

20

(Method 2)

In the second embodiment, where the polyquinoline is prepared having end groups that may be later transformed into the desired acetylene end groups, the procedure is the same as for Method 1, except that the endcapper (AE" or BE") is added to the polymer dope after the desired MW is reached but before the polymer is coagulated.

In general, it is preferable to add the endcapper after the polymerization reaction is complete (i.e., Method 1 rather than Method 2) to avoid potential side reactions. Since the polymer is not isolated and purified before adding endcapper in either Method 1 or Method 2, the overall cost of the process is essentially the same.

GENERAL PROCEDURE

Nucleophilic Displacement Polymerization

In the first embodiment, where the endcapper incorporating the acetylene function is added to the polymerization

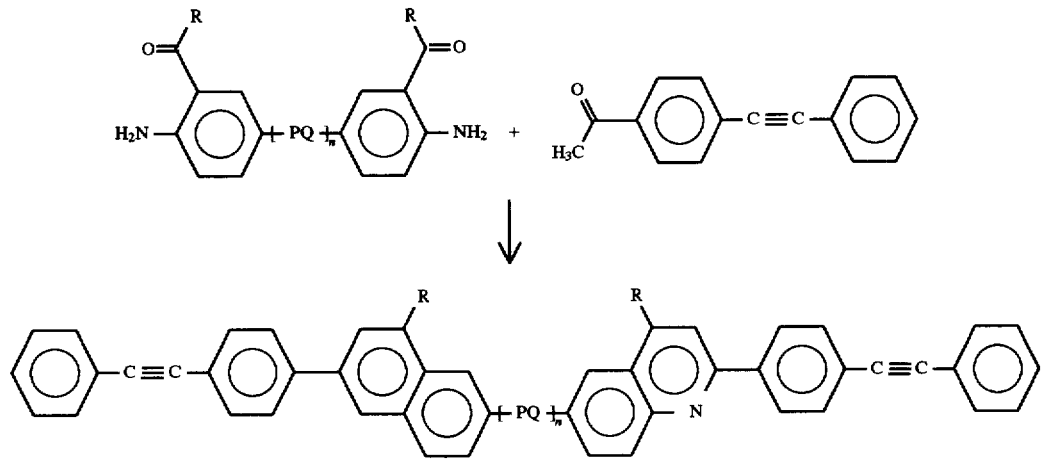

GENERAL PROCEDURE

Friedlander Polymerization (Method 1)

In the first embodiment, where the endcapper incorporating an acetylene group is added to the polymerization reaction, the appropriate monomers are selected from a bis-methylene ketone (AA), bis-amino carbonyl (BB), and methylene ketone amino carbonyl (AB) compound and added to a catalyst and a solvent. The molar amounts of monomers are selected to obtain the desired MW using, for example, the Carothers equation. The absolute amounts are selected to give a product polymer solution of between 1% and 50% by weight, preferably about 25% by weight. If the catalyst is butyl acid phosphate, no other solvent is necessary. However, solvent such as toluene or meta-cresol may be used. The endcapper (AE" or BE") is added in an amount as determined, for example, by the Carothers equation and is consistent with the amounts of monomers. The mixture is then heated to about 110° C. for about 3 hours and then at about 90° C. until the desired MW is achieved as measured by gel permeation chromatography or other suitable method. The mixture is cooled to room temperature and coagulated into a non-solvent such as ethanol. A base such as triethylamine (10% to 15% by volume) may be added to neutralize the acid catalyst. The solid is collected by filtration, washed, and dried.

reaction, the amounts of selected monomers (AA, AB, and/or BB) to be used and the endcapper (AE" or BE") are calculated using the Carothers equation or other method (for example, empirically). The monomers are placed in a reactor with a slight molar excess of potassium carbonate (or similar base), anhydrous solvent, and a solvent which forms an azeotrope with water. The anhydrous solvent may be an amide solvent, such as NMP, and the azeotropic solvent may be an aromatic solvent, such as toluene. The amounts of monomers should be selected such that the product polymer solution is about 1% to 50% by weight polymer; preferably, about 20%. The mixture is heated to about 180° C. for about 5 hours, during which time water is removed by azeotropic distillation. The temperature is then raised to about 200° C. for 12 to 24 hours or until the desired MW is reached as measured by gel permeation chromatography or other suitable method. The mixture is cooled to room temperature, and the endcapper (AE" or BE") and a slight molar excess of anhydrous potassium carbonate over the endcapper are added. The mixture is then stirred at about 80° C. for about 24 to 72 hours. It is then cooled to room temperature and coagulated by pouring into water, filtered, washed, and dried.

The endcapper may also be added at the same time as the monomers if the acetylene functional group is known not to react under the polymerization conditions. Since high temperatures (200° C.) are used, this will be possible only for relatively unreactive acetylene, such as phenylethynylbenzenes.

In the second embodiment, where the polyquinoline is prepared having end groups that may be later transformed into the desired acetylene end groups, a polyquinoline is formed by any method such that the end groups are complementary to an endcapper. The polyquinoline is dissolved in a suitable solvent, in the range of 1% to 50% by weight, preferably about 25% by weight, and the endcapper is added, along with any catalyst, acid, or base which might be required. The mixture is heated to effect the endcapping reaction, and the resulting endcapped polymer is isolated by coagulation into a non-solvent. The endcapped product polymer may be washed, further purified by extraction or re-coagulation if desired, and dried.

In one embodiment, thermosetting polyquinolines of the present invention are prepared in powder or pellet form (uncured), for example by precipitation from solution with a non-solvent, and the powder is molded by application of heat and, if necessary, pressure. The molding operation may be compression molding, injection molding, extrusion, or other means of applying heat and pressure. As the powder is heated, it is desirable for the particles to soften and flow to the extent that they fill all available space and adhere permanently to one another. In order to cause flow at reasonable pressures, plastics must be heated above their $T_g$ (or, if highly crystalline, above their melting temperature, $T_m$). The $T_g$ and $T_m$ depend on the structure (flexibility) of the polymer chain, the molecular weight, and any plasticizers or additives. In order to form a cross-link, two or more cross-linking groups must come in contact. It is therefore important to heat the uncured endcapped polymer to above the $T_g$ (or $T_m$) so that individual cross-linking groups can diffuse together. It is preferable for the cross-linking reaction to occur at least about 50° C. above the $T_g$ (or $T_m$), more preferably, at least about 75° C. above $T_g$ (or $T_m$), and, most preferably, at least about 100° C. above $T_g$ (or $T_m$).

The curing temperature should not be so high that thermal degradation becomes a problem. Thermal degradation can be measured by Thermal Gravimetric Analysis (TGA) wherein a sample is slowly heated in a controlled atmosphere and continuously weighed. The lowest possible curing temperature is desirable to minimize the temperature requirements of the processing equipment, and to minimize dimensional change and stress do to contraction on cooling after cure.

The reactivity of the acetylene function (E") is largely controlled by steric factors. Larger substituents R will slow the cross-linking reaction and a higher curing temperature will be necessary. For any particular type of acetylene function, ethynyl, ethynylarylene, propargyl, or propargyl arylene, the unsubstituted acetylenes (that is, R=H) will have the lowest curing temperature. Alkyl or aryl substituents will increase the curing temperature. Aryl and heteroaryl substituents are preferred because of their high thermal stability. For example, phenylethynyl endcapped polyimides are typically cured at 350° C. to 400° C., while ethynyl endcapped polyimides are typically cured at 200° C. to 250° C. End caps with R groups, such as methyl and ethyl, which are intermediate in size, will cure at intermediate temperatures.

The $T_g$ of polyquinolines and the reaction of cross-linking endcappers may both be measured by Differential Scanning Calorimetry (DSC). Both $T_g$ (and/or $T_m$) and cure exotherm $T_{ex}$ may be seen on a single DSC run. In this way, it is easy to check the temperature difference between $T_g$ and $T_{ex}$. Since $T_g$ depends on MW, i.e., for a given polymer, a lower MW results in a lower $T_g$, it is often possible to obtain the desired temperature difference between $T_g$ and $T_{ex}$ with a given end group by adjusting the MW. For example, if a particular polyquinoline/end group combination has a MW of 65,000, a $T_g$ of 260° C., and a $T_{ex}$ of 240° C., a better curing system would be expected for a lower MW polymer. One approach for determining the desired MW of the thermosetting polymer of the present invention is to prepare a series of polyquinolines having MWs of about 40,000, 20,000 and 10,000 with the same reactive end group E". DSC traces should then be taken for each polyquinoline. These experiments will reveal the relationship between $T_g$ and MW and allow a choice of the best MW. Additional samples with other MWs may be run to further define the range of acceptable MW.

The MW may also be optimized by heating (under a pressure which simulates the desired processing method) small amounts (1 to 10 grams is convenient, but more or less may be used) of samples of various MWs. If $T_{ex}$ is too low relative to $T_g$, the samples will remain powdery. The sample with optimal MW is that which has the highest MW which still flows enough to consolidate on heating.

A determination of the desired curing time for cross-linking the thermosetting polyquinolines of the present invention can be made empirically. For example, one method of determining the desired curing time is to heat a selected number of small (0.1 to 1 g) samples of the polymer for various times at a selected temperature. After each of the samples has been heated for the selected time, the exotherm area of the sample is determined by differential scanning calorimetry. The curing time is the time necessary to reduce the exotherm area, i.e., the area under the curve, to a given percentage of the value of a sample that has not been heated. For example, one might select a curing time at a given temperature as being the time necessary to reduce the exotherm area to 25% of the value for a sample that has not been heated, or may select the time necessary to reduce the exotherm area to 10% of the value of a sample that has not been heated.

In one exemplary embodiment of practice of the present invention, the endcapped polymers of the present invention are heated until they are insoluble in N-methylpyrrolidinone. In another embodiment, it is determined that the polymer should be heated until at least one-half of the end groups have reacted. In this instance, the time required to react one-half of the end groups would be determined by differential scanning calorimetry as the point at which the exotherm area has been reduced to 50% of the value of a sample that has not been heated.

Once cured, thermosetting polymers of the present invention are insoluble in common solvents, such as toluene, ethanol, jet fuel, hydraulic fluids, and the like. Furthermore, the R groups can be chosen such that the cross-linked polymers are stable at temperatures of from about 250° C. to 350° C. or higher.

In addition to heat curing, the thermosetting polyquinolines of the present invention can be cured by ultraviolet radiation using conventional radiation equipment.

The thermosetting polyquinolines of the present invention may be cured as neat polymers, or additives and/or fillers may be included. Additives include but are not limited to adhesives, adhesion promoters, pigments, dyes, UV stabilizers, anti-oxidants, plasticizers, lubricants, mold release agents, flame retardants, tougheners, anti-static agents, blowing agents, and curing agents. Fillers include but are not limited to silica, carbon black, graphite, titania, alumina, mica, talc, calcium carbonate, metal powders, glass micro-balloons, plastic micro-balloons, fibers of glass, titania, carbon, graphite, and polymers such as polyethylene fibers, poly(phenyleneterephthalamide) fibers, and poly (phenylenebenzobisoxazole) fibers.

The thermosetting polyquinolines of the present invention may be blended with other polymers before curing. Non-limiting examples of blend partners include polyimides, polysilanes, silicones, polyphenylene oxide, polyphenylene sulfide, polyetherimide, polypropylene oxide, polycarbonate, polyethylene oxide, polystyrene, polyetherketone, polyetheretherketone, polyamides, polyurethanes, epoxy resins, cyanate ester resins, bis-maleimide resins, and phenolic resins.

The thermosetting polyquinolines of the present invention may be dissolved in a suitable solvent and cast into free-standing films or coated onto substrates.

Non-limiting examples of substrates onto which the thermosetting polyquinolines of the present invention may be coated are selected from the group consisting of aluminum, aluminum nitride, copper, diamond, quartz, silica, silicon, gallium arsenide, silicon carbide, gold, solder, and titanium. Multiple layers of the thermosetting polyquinolines may be present on any one such substrate.

In one exemplary embodiment of practice of the present invention, a solution of thermosetting polyquinolines having solids content of 1% to 60%, preferably 5% to 40%, and more preferably 10% to 30%, may be spin coated onto a silicon wafer and dried and cured by application of heat. The silicon wafer may have circuitry fabricated onto its surface, as is known in the art of integrated circuit manufacture, or it may have previously coated metal lines and insulators interconnecting underlying integrated circuits, or it may be a bare wafer, either etched, oxidized, or otherwise treated. Adhesion promoters may be applied to the wafer prior to coating the polyquinoline.

The application of heat may be heating to a single pre-set temperature for a fixed time, or it may be a more complex thermal cycle designed to remove solvent and effect curing in several stages. Such heat cycles may be determined empirically for a given polyquinoline thermoset and a given application, as is commonly practiced in the art.

The thermosetting polyquinolines of the present invention may be coated onto objects or substrates by any method known in the art including, but not limited to, spray coating, plasma coating, dip coating, spin coating, brushing, curtain coating, or by lamination of a previously prepared film. Drying and curing may then be carried out in separate steps or in a single operation.

The following specific examples are illustrative of the present invention, but are not considered limiting thereof in any way.

EXAMPLE 1

Preparation of a difluoroquinoline monomer (6,6'-bis-[2-(4-fluorophenyl)-4-phenylquinoline]) of the following structure by condensing bis-aminobenzene derivatives

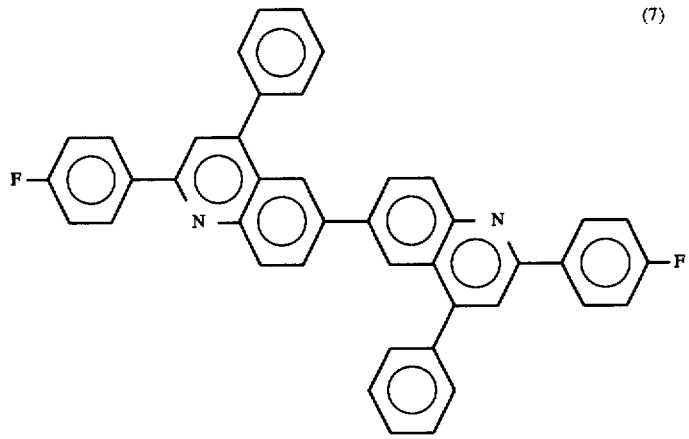

(7)

A 10 ml round-bottom flask was loaded with 1 g (2.56 mmol) 4,4'-diamino-3,3'-benzoylbiphenyl 0.4 g (2.89mmol) 4-fluoroacetophenone and 0.1 g (0.52 mmol) toluene-sulfonic acid monohydrate. The open flask was heated to about 200° C. A color change from bright yellow to orange was apparent during the reaction, and water evaporated. Continuous heating at 200° C. caused the product to crystallize. The flask was cooled and the crude solid was crushed and washed with hot ethanol. Further recrystallization gave monomer (7) with an 84% yield.

EXAMPLE 2

Preparation of Activated Zinc Dust

Activated zinc dust is obtained after two washings of commercially available 325 mesh zinc dust with 1M hydrogen chloride in diethyl ether (anhydrous) followed by two washings with diethyl ether (anhydrous) and drying in vacuo or under inert atmosphere for several hours at about 100°–200° C. If clumps form during drying, the zinc dust is re-sieved to −150 mesh. This material should be used immediately or stored under an inert atmosphere away from oxygen and moisture.

EXAMPLE 3

Preparation of 6,6'-bis[2-(4-fluorophenyl)-4-phenylquinoline] (Monomer 7) by coupling preformed chlorofluoroquinolines.

A 250 mL, three-necked, round-bottomed flask fitted with a nitrogen inlet, a stirring rod set up, and a distillation unit was charged with 2-amino-5-chlorobenzophenone (17.38 g, 75.0 mmol), 4'-fluoroacetophenone (10.0 mL, 82.0 mmol), and p-tosic acid (1.00 g, 5.3 mmol). The reaction was heated to 180° C. under nitrogen (16 h) and water removed by distillation. To the reaction was added 0.726 g K$_2$CO$_3$ and toluene (2×50 mL) was successively added to the reaction mixture and removed through the distillation set up to assure removal of the last traces of water.

The structure of the propargyl endcapped poly[(6,6'-bis-4-phenylquinoline-2,2'diyl)-,1,4-phenyleneoxy-1,4-phenylene-hexafluoroisopropylidene-1,4-phenyleneoxy-1,4-phenylene] is shown below:

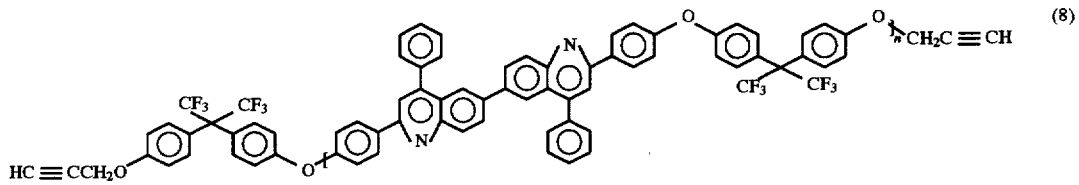
(8)

The reaction was cooled to room temperature and a mixture containing bis(triphenylphosphine) nickel dichloride (0.681 g, 1.04 mmol), sodium iodide (1.40 g, 9.37 mmol), triphenylphosphine (8.19 g, 33.3 mmol), and activated zinc dust (3.13 g, 47.9 mmol) were added to the reaction flask along with NMP (86 mL). The flask was heated under nitrogen to 70° C. (16 h). The mixture was diluted with NMP (10 mL), the temperature was raised to 170° C., and the mixture was filtered through Celite. The mother liquor was cooled to −20° C. and the product was collected by filtration. The yellow solid was washed with cold ethanol/methylene chloride (3/1) and was dried in a vacuum oven at 100° C. Yield of monomer (7) was 18.03 g, 80.5%.

EXAMPLE 4

Preparation by nucleophilic displacement of Propargyl Ether Endcapped Poly[(6,6'-bis-4-phenylquinoline-2,2'diyl)-1,4-phenyleneoxy-,1,4-phenylene-hexafluoroisopropylidene-1,4-phenyleneoxy-1,4-phenylene].

One-step method.

To a 100 ml three-necked, round-bottom flask equipped with a nitrogen inlet, mechanical stirrer, and a Dean-Stark trap with a condenser was placed 1.404 g (2.353×10$^{-3}$ mole) difluoroquinoline (7), 1.000 g (2.974×10$^{-3}$ mole) bisphenol AF, 0.715 g (5.17×10$^{31\ 3}$ mole) K$_2$CO$_3$, 10 ml anhydrous NMP, and 2 ml toluene. The reaction mixture was heated to 150° C. for 5 hours (dehydration) and then the temperature was increased to 200° C. and held for 24 hours. After cooling to room temperature, 0.285 g (2.400×10$^{31\ 3}$ mole) propargyl bromide (CH≡CCH$_2$Br) and 0.331 g (2.396×10$^{-3}$ mole) K$_2$CO$_3$ were added. The solution was stirred at 80° C. for 3 days. After cooling to room temperature the solution was poured into 200 ml methanol. The product was collected by filtration and then treated with boiling water to remove any trapped salts. The polymer was dried in a vacuum oven at 100° C. overnight.

EXAMPLE 5

Preparation by nucleophilic displacement of Propargyl Ether Endcapped Poly[(6,6'-bis-4-phenylquinoline-2,2'diyl)-1,4-phenyleneoxy-1,4-phenylene-hexafluoroisopropylidene-1,4-phenyleneoxy-1,4-phenylene]. Two-step method.

First Step

Hydroxy Endcapped Polyquinoline

To a 100 ml three-necked, round-bottom flask equipped with a nitrogen inlet, a mechanical stirrer, and a Dean-Stark trap was placed 2.801 g (4.909×10$^{-3}$ mole) difluoroquinoline (7), 2.000 g (5.948×10$^{-3}$ mole) bis-phenol AF, 1.430 g (10.34×10$^{-3}$ mole) K$_2$CO$_3$, 20 ml anhydrous NMP and 4 ml toluene. The reaction mixture was heated to 150° C. for 5 hours (dehydration) and then to 200° C. for 24 hours. After cooling to room temperature, the mixture was poured into methanol and collected by filtration. The product was boiled in water to remove trace salts. The polymer was dried in a vacuum oven overnight. The structure of the polymer is shown below:

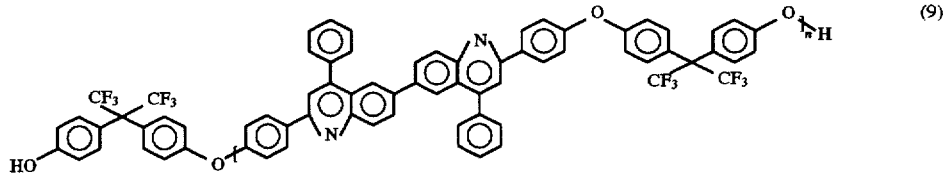
(9)

Second Step

Propargyl Endcapped Polyquinoline

To a 50 ml three-necked, round-bottom flask equipped with a nitrogen inlet, a mechanical stirrer, and a condenser was placed 1.000 g (10.250×10$^{-3}$ mole) hydroxy endcapped polyquinoline polymer (9), 0.119 g (1.000×10$^{-3}$ mole) propargyl bromide, 0.138 g (1.000×10$^{-3}$ mole) K$_2$CO$_3$ and 5 ml toluene. The reaction mixture was heated at 80° C. under nitrogen for 3 days. It was then cooled to room temperature and poured into methanol. The polymer was collected by filtration. The product was washed twice with methanol and dried in a vacuum oven at 100° C. overnight. The M$_n$ by GPC relative to polystyrene standards was 10,340.

EXAMPLE 6

Preparation by nucleophilic displacement of Propargyl Ether Endcapped Poly[(6,6'-bis-4-phenylquinoline-2,2'diyl)-1,4-phenyleneoxy-1,4-phenylene-isopropylidene-1,4-phenyleneoxy-1,4-phenylene]. Two-step method First Step Hydroxy Endcapped Polyquinoline To a 100 ml three-necked, round-bottom flask equipped with a nitrogen inlet, a mechanical stirrer and a Dean-Stark trap is placed 2.801 g (4.909×10$^{-3}$ mole) difluoroquinoline (7), 2.000 g (5.948×10$^{-3}$ mole) bisphenol A, 1.430 g (10.34× 10$^{-3}$ mole) K$_2$CO$_3$, 20 ml anhydrous NMP and 4 ml toluene. The reaction mixture is heated to 150° C. for 5 hours (dehydration) and then to 200° C. for 24 hours. After cooling to room temperature, the mixture is poured into methanol and collected by filtration. The product is boiled in water to remove trace salts. The polymer is dried in a vacuum oven overnight. The structure of the polymer is shown below:

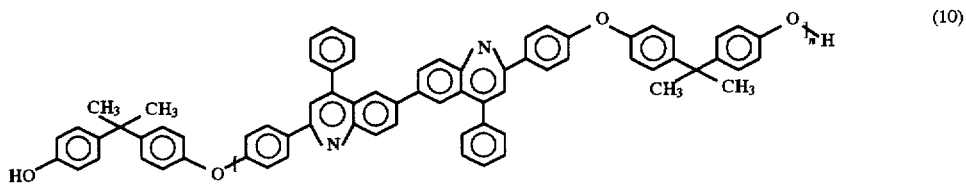

Second Step

Propargyl Endcapped Polyquinoline

To a 50 ml three-necked, round-bottom flask equipped with a nitrogen inlet, a mechanical stirrer, and a condenser is placed 1.000 g (10.250×10$^{-3}$ mole) hydroxy endcapped polyquinoline polymer (10), 0.119 g (1.000×10$^{-3}$ mole) propargyl bromide, 0.138 g (1.000×10$^{-3}$ mole) K$_2$CO$_3$ and 5 ml toluene. The reaction mixture is heated at 80° C. under nitrogen for 3 days. It is then cooled to room temperature and poured into methanol. The polymer is collected by filtration. The product is washed twice with methanol and dried in a vacuum oven at 100° C. overnight.

The structure of the propargyl endcapped poly[(6,6'-bis-4-phenylquinoline-2,2'diyl)-1,4-phenyleneoxy-1,4-phenylene-isopropylidene-1,4-phenyleneoxy-1,4-phenylene] is shown below:

EXAMPLE 7

Preparation of Propargyl Endcapped Polyquinoline (8) with Molecular Weight of Approximately 5K A 100 ml three-necked, round-bottom flask was charged with 1.4040 g (2.353×10$^{-3}$ moles) of difluoroquinoline (7), 1.0000 g (2.974×10$^{-3}$ moles) of bisphenol AF, 0.7148 g (5.17×10$^{-3}$ moles) of K$_2$CO$_3$, 10 ml anhydrous NMP, and 2 ml of toluene. The flask was equipped with a mechanical stirrer, nitrogen inlet, and a short path distillation apparatus for water removal. The reaction mixture was heated at 180° C. for 5 hours (dehydration) and then to 200° C. for 24 hours. After cooling to room temperature, 0.28552 g (2.4× 10$^{-3}$ moles) of propargyl bromide and 0.3312 g of K$_2$CO$_3$ were added. The solution was stirred at 80° C. for 3 days. The reaction mixture was cooled to room temperature and poured over 200 ml of water. The product was collected by filtration and washed twice with water. The product polymer was dried at 100° C. under vacuum for 17 hours. The M$_n$ by GPC relative to polystyrene standards was 5017.

EXAMPLE 8

Preparation of Fluorine-terminated Polyquinoline (12) from 6,6'-bis[2-(4-fluorophenyl)-4-phenylquinoline] (7) and bis-phenol AF

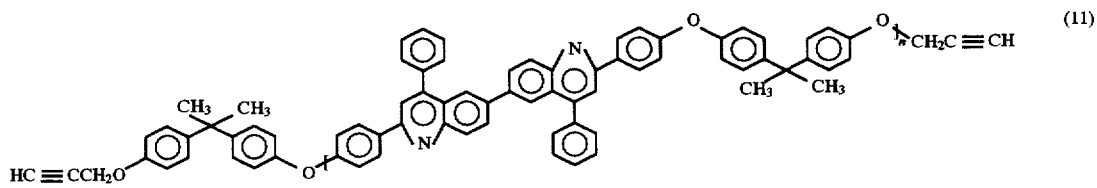

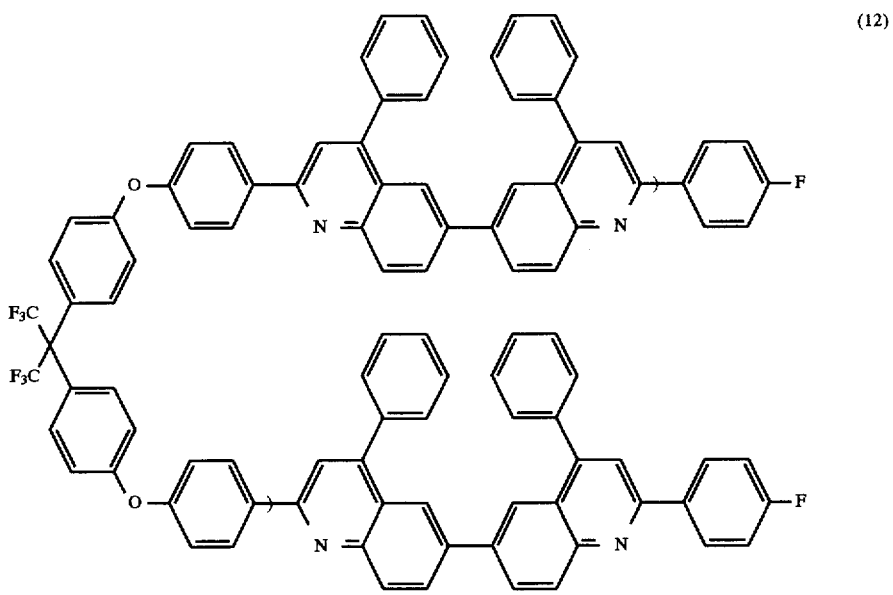

(12)

A 100 ml, three-necked, round-bottom flask fitted with a Dean-Stark trap containing a condenser with a nitrogen inlet valve and a stirring rod assembly was charged with 3.1739 g (5.318 mol) of 6,6'-bis[2-(4-fluorophenyl)-4-phenylquinoline] (7), 1.6867 g (5.017 mmol) of bis-phenol AF, 1.04 g (7.5 mol) of potassium carbonate, 20 ml of N-methylpyrrolidinone (NMP), and 20 ml of toluene. The mixture was heated to reflux and allowed to stir under nitrogen for 16 hours. The toluene and final traces of water were removed through the Dean-Stark apparatus, and the solution was stirred at reflux for an additional 18 hours. The mixture was diluted with 20 ml of NMP and cooled to room temperature. The diluted dope was coagulated in 160 ml of acetone. The polymer was collected by filtration, dissolved in 40 ml of NMP, and coagulated a second time in 160 ml of deionized water. The polymer was filtered, boiled in 50 ml of acetone, filtered again, and dried in a vacuum oven at 140° C. for 12 hours. Yield 4.32 g (93%). $MW_n$=19,800 by GPC (versus polystyrene standards).

EXAMPLE 9

Preparation of an α-methylketone terminated oligomer from 2,2'-bis-[4-(4-acetylphenoxy)phenyl]hexafluoropropane and 3,3'-dibenzoyl-4,4'-diamino-biphenyl with approximate MW=15,000
(Oligomer I)

A 500 ml, three-necked, round-bottom flask fitted with a nitrogen inlet valve is charged with 19.69 g of 3,3'-dibenzoyl-4,4'-diaminobiphenyl, 32.06 g of 2,2'-bis[4-(4-acetylphenoxy)phenyl]hexafluoropropane, and 204 g of n-butyl acid phosphate. The mixture is heated at 110° C. for 3 hours and then at 90° C. for 82 hours under nitrogen. The mixture is cooled to room temperature and is coagulated in a 15% triethylamine/ethanol solution. The precipitate that formed is collected by filtration and boiled in a 10% triethylamine/ethanol solution. The solid is again collected by filtration and dried in a vacuum oven at 120° C. The molecular weight can be varied by changing the relative amounts of the monomers.

EXAMPLE 10

Geminal Dichlorination of Keto Groups of the Polymer of Example 9 and Conversion to the Corresponding Acetylene Terminated Oligomer A 500 ml, three-necked, round-bottom flask fitted with a condenser containing a nitrogen inlet valve is charged with 40 g of the polymer of Example 9 and 200 ml of thionyl chloride. The mixture is heated under nitrogen at reflux for 16 hours. The mixture is cooled and the excess thionyl chloride is distilled from the reaction flask. To the flask is added 200 ml of anhydrous dimethylsulfoxide and 50 g of potassium tert-butylphenoxide, and the mixture is heated at reflux overnight. The reaction is cooled to room temperature and the resulting polymer is coagulated in a 50% ethanol/deionized water mixture. The polymer precipitate is collected by filtration and dried in a vacuum oven. The structure of the polymer is shown below:

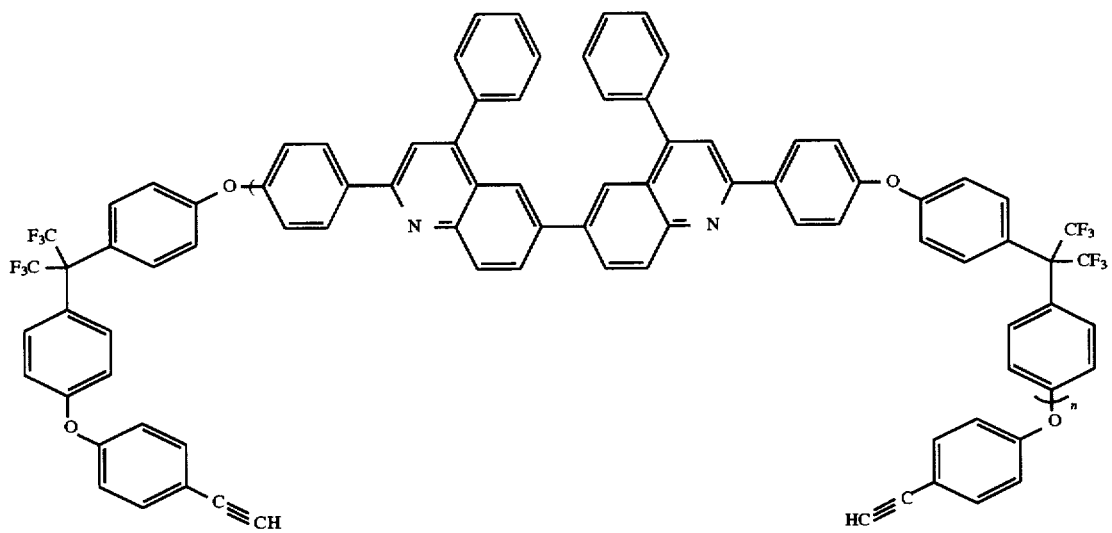

(13)

where n is the number of repeat units.

EXAMPLE 11

Preparation of 1-Phenyl-2-(4-acetophenyl)ethyne (4-phenylethynylacetophenone)

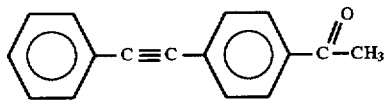
(14)

A 500 ml, three-necked, round-bottom flask fitted with a stirring rod assembly and a condenser containing a nitrogen inlet valve is charged with 21.9 g of 4'-bromoacetophenone, 11.0 phenylacetylene, 0.2 g of triphenylphosphine, 0.1 g of cuprous iodide, and 450 ml of triethylamine. The mixture is heated at reflux for 4 hours and then cooled to room temperature and stirred for an additional 16 hours. The mixture is poured into a 1% aqueous hydrogen chloride solution, and the resulting precipitate is collected by filtration. The compound is purified by recrystallization, and the solid is dried in a vacuum oven.

EXAMPLE 12

Preparation of an α-Aminoketone Terminated Oligomer from 2,2'-bis[4-(4-acetylphenoxy)phenyl] hexafluoropropane and 3,3'-dibenzoyl-4,4'-diamino-biphenyl with Approximate MW=15,000 (Oligomer 2)

A 500 ml, three-necked, round-bottom flask fitted with a nitrogen inlet valve was charged with 21.977 g of 3,3'-dibenzoyl-4,4'-diaminobiphenyl, 28.738 g of 2,2'-bis[4-(4-acetylphenoxy)phenyl]hexafluoropropane, and 204 g of n-butyl acid phosphate. The mixture was heated at 110° C. for 3 hours and then at 90° C. for 82 hours under nitrogen. The mixture was cooled to room temperature and was coagulated in a 15% triethylamine/ethanol solution. The precipitate that formed was collected by filtration and was boiled in a 10% triethylamine/ethanol solution. The solid was again collected by filtration and was dried in an oven at 120° C. Yield 42.7 g (91%).

EXAMPLE 13

Preparation of the derivative of the polymer of Example 12 having end groups with an acetylene functionality.

A 500 ml, three-necked, round-bottom flask fitted with a nitrogen inlet valve is charged with 100 g of the polymer of Example 12, 44.05 g of 1-phenyl-2-(4-acetophenyl)ethyne, and 200 g of n-butyl acid phosphate. The mixture is heated at 110° C. for 48 hours under nitrogen. The mixture is cooled to room temperature and is coagulated in a 15% triethylamine/ethanol solution. The precipitate that formed is collected by filtration, boiled in a triethylamine/ethanol solution, and dried in a vacuum over at 120° C. The structure of the polymer is shown below:

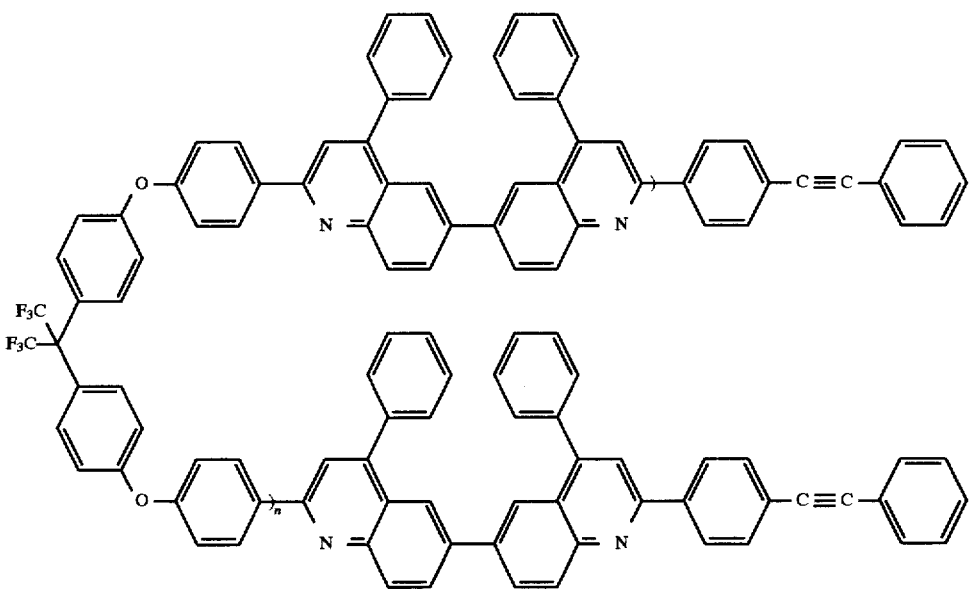

(15)

where n is the number of repeat units.

EXAMPLE 14

A 2" by 2" square mold is filled to about 0.2" with the powder form (as precipitated) of the propargyl ether end-capped polymer of Example 4. The mold is pressed in a heated hydraulic press at 500 psi and 250° C. and held under pressure for 2 hours. After cooling to below 100° C., the pressure is released and the product square panel released from the mold.

The product is cured, and the cured polymer is less soluble and is resistant to higher temperatures than before curing.

EXAMPLE 15

A 15% by weight solution is made of the propargyl ether endcapped polymer of Example 4 in dimethylacetamide (DMAc). Glass fiber fabric is impregnated with polymer by dip-coating in the solution and drying under vacuum at 120° C. overnight. The dry impregnated fabric is draped over a male mold and covered with high temperature polymer film bagging material. The entire mold assembly is placed into an autoclave and held at 200 psi and 200° C. for 5 hours. The part is removed from the autoclave and post-cured at atmospheric pressure and 300° C. for 2 hours. The product part is then separated from the mold and hand finished.

EXAMPLE 16

A film of the polymer of Example 4 is cast from a 10% solution in cyclopentanone onto a glass plate. After air-drying for 1 hour, the film is dried in an oven at 100° C. for 2 hours. The film is then cross-linked by exposing it to ultra-violet light at 254 nm for 2 hours. Such cross-linked films have good thermal stability and solvent resistance.

EXAMPLE 17

Preparation of poly(4',4"-(2,4-diphenylquinoline)diyl -oxy-1,4-phenylene-isopropylidene-1,4-phenylene-oxy). (19)

3-(4-fluorophenyl)-2,1-benzisoxazole. (16)

A total of 50.7 g (0.375 mol) of 4-fluorophenyl-acetonitrile is slowly added to a vigorously stirred, room-temperature solution of 150 g (3.75 mol) of sodium hydroxide in 750 ml of absolute methanol. After solution is complete, 46 g (0.374 mol) of nitrobenzene is slowly added. The resulting solution is warmed to 65°–70° C. and held at this temperature for 9 hours. The dark slurry is cooled to room temperature, diluted with 250 ml of 50% methanol, and cooled in an ice bath. The resulting dark precipitate is filtered and washed with cold methanol until the methanol washings were clear. The product (16) is recrystallized from toluene.

2-amino-4'-fluorobenzophenone. (17)

To a suspension of (16) (42.6 g, 0.2 mol) in 750 ml of dry tetrahydrofuran (THF) and 20 ml of triethylamine is added 5% palladium on charcoal (6 g). The vigorously stirred suspension is flushed with hydrogen gas and stirred at room temperature under a hydrogen atmosphere until absorption of hydrogen ceases (approximately 90–90% of the molar amount; 8–10 hours). The catalyst is removed by filtration through a bed of celite, and the solvent is removed under reduced pressure. The product (16) is recrystallized from toluene.

2,4-bis(4-fluorophenyl)quinoline. (18)

A flask is loaded with (17) (21.5 g, 0.1 mol), 4-fluoroacetophenone (13.8 g, 0.1 mol), and toluene sulfonic acid monohydrate (3.8 g, 0.02 mol). The flask is heated to 200° C. and the water of condensation removed. After water evolution ceased, the mixture is cooled and the crude solid product is crushed and washed with hot ethanol The product is further recrystallized from toluene.

Polymer. (19)

A 100 ml three-necked, round-bottom flask is charged with 3.0147 g (9.5 mmol) of (18), 2.2829 g (10 mmol) of bisphenol A, 2.75 g of $K_2CO_3$, 30 ml anhydrous NMP, and 6 ml of toluene. The flask is equipped with a mechanical stirrer, nitrogen inlet, and a short path distillation apparatus for water removal. The reaction mixture is heated at 180° C. for 5 hours (dehydration) and then to 200° C. for 24 hours. After cooling to room temperature, 0.0119 g (1 mmol) propargyl bromide and 0.138 g (1 mmol) $K_2CO_3$ are added.

The mixture is stirred at 80° C. under nitrogen for three days. After cooling to room temperature, the reaction mixture is poured over 200 ml of water. The product is collected by filtration and washed twice with water. The product polymer is dried at 100° C. under vacuum for 16 hours. The polymer repeat unit has the following structure:

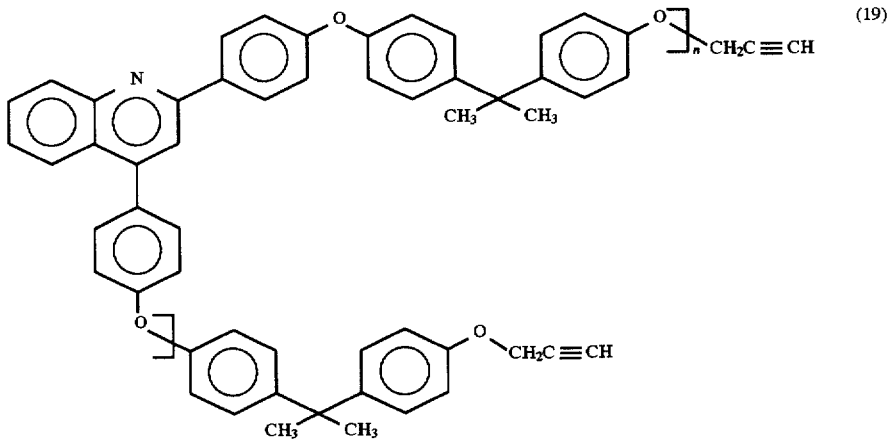

The number average molecular weight of the polymer is about 10,000.

EXAMPLE 18

Differential Scanning Calorimetry of Thermosetting Polyquinolines

DSC was used to determine the $T_g$ and cross-linking temperature $T_{ex}$ of polymers prepared in accordance with Examples 5 and 7. The results are presented in Table 1.

TABLE 1

| Polymer | | Mn | $T_g$ | DSC Exotherm | |
|---|---|---|---|---|---|
| Ex | Endcap | (GPC) | °C. | Onset °C. | Maximum °C. |
| Ex 5 | Propargyl | 10340 | 217 | 230 | 310 |
| Ex 7 | Propargyl | 5017 | 153 ($T_m$) | 230 | 310 |

Turning to FIG. 1, there is shown a DSC trace for the propargyl endcapped polymer prepared in accordance with Example 7. The polymer appears to have a $T_g$ at about 110° C. seen as a sharp rise in baseline, a $T_m$ at about 153° C., and an exotherm with an onset temperature of about 230° C. The level area between the positive peak at 153° C. ($T_m$) and the large negative peak at 310° C. (exotherm maximum) is the processing window.

Turning to FIG. 2, there is shown a DSC trace for the propargyl endcapped polymer prepared in accordance with Example 5. The $T_g$ of the polymer appears at approximately 217° C. as a shoulder and a large negative exotherm is seen with an onset at about 230° C. and a maximum at about 310° C. The processing window for the Example 5 polymer is much more narrow than the polymer produced in Example 7.

Note that the temperature scales on FIGS. 1 and 2 are not the same.

The propargyl endcapped polymers were tested for consolidation by applying both elevated temperature and pressure. The following cure cycle was used: 30 min at 200° C., 30 min at 350° C. and ballistic cooling to 150° C. The material prepared in accordance with Example 5 appeared powdery. Examination under the microscope showed a foam like structure indicating that the resin may have flowed and then foamed due to gas formation. A second sample of the Example 5 material was heated only to 200° C. to see if foaming could be avoided. This sample did not consolidate at all, suggesting that it would at best be difficult to find conditions for processing the Example 5 polymer.

The sample polymer provided in accordance with Example 7 using the same cure cycle as with the Example 5 material provided a clear, but dark, consolidated plaque. The Example 7 material also showed flow behavior at 200° C., a temperature at which curing is not expected to occur.

The above description of preferred embodiments of thermosetting polyquinolines and the methods for producing such polyquinolines are for illustrative purposes. Because of variations which will be apparent to those skilled in the art, the present invention is not intended to be limited to the particular embodiments described above. The invention disclosed herein may suitably be practiced in the absence of any material or composition which is not specifically disclosed herein. The scope of the invention is defined in the following claims.

What is claimed is:

1. A polymer comprising quinoline repeat units and end groups comprising an acetylene functionality.

2. The polymer according to claim 1 wherein the end group is selected from the group consisting of: —C≡CR, —Ar—C≡CR, —CH₂C≡CR, —Ar—OCH₂C≡CR, and —OCH₂C≡CR, wherein R is H, alkyl, aryl or heteroaryl, and Ar is arylene or heteroarylene, where Ar may be optionally substituted with alkyl, aryl, alkoxy, aryloxy, chloro, fluoro, fluoroalkyl, fluoroaryl, and nitro, and R may be optionally substituted with alkoxy, aryloxy, chloro, fluoro, fluoroalkyl, fluoroaryl, and nitro.

3. The polymer according to claim 1 comprising end groups selected from the group consisting of —OCH₂C≡CH, —OCH₂C≡CCH₃, —C≡CH, —C≡CC₆H₅, —C≡C—C₆H₄O₆CH₅, —C≡CCH₃.

4. The polymer according to claim 1 comprising end groups selected from the group consisting of —C₆H₄—C≡CH;

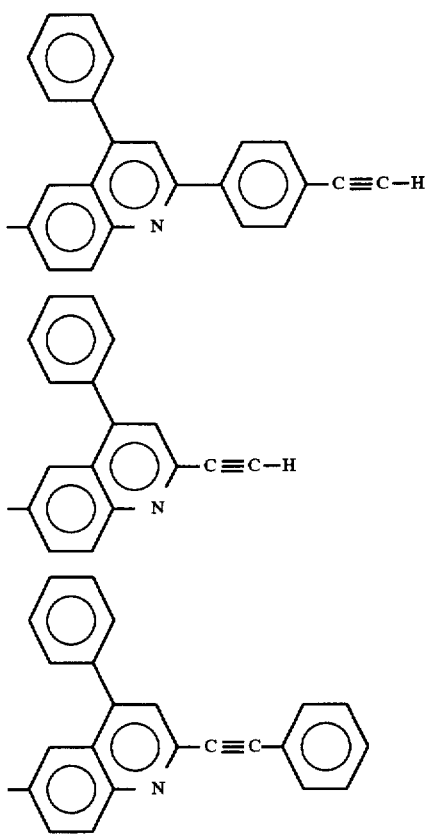

—C₆H₄—OCH₂C≡CH, —C₆H₄—OCH₂C≡CCH₃; and —C₆H₄—OCH₂C≡CC₆H₅.

5. The polymer according to claim 2 wherein Ar is selected from the group consisting of 1,4-phenylene, 1,3-phenylene, 2-methyl-1,4-phenylene, 1,4-naphthylene, 4,4'biphenylene, 2,4-pyridinediyl, 2,4-quinolinediyl, 2,6-quinolinediyl, 4-phenyl,-2,6-quinolinediyl, and 3,6-quinolinediyl.

6. The polymer according to claim 1 wherein the quinoline repeat units have the structure:

wherein Y is a divalent moiety selected from the group consisting of —O— and —O—W—O, wherein W is a divalent group selected from the group consisting of:

—Ar'— (where Ar' means arylene),

—Het— (where Het means heteroarylene),

—Ar'—O—Ar'—,

—Ar'—C(O)—Ar'—,

—Ar'—S—Ar'—,

—Ar'—S(O)—Ar'—,

—Ar'—S(O)₂—Ar'—, and

—Ar'—Q—Ar'—,;

and wherein

Q is a divalent group containing a quaternary carbon as shown below:

Q=

U, U'=—CH₃, —CF₃, Ar, or bridging where if U and U' are bridging, they may be alkyl, aryl, alkaryl, ether, ester, amide, alkyl ketone, aryl ketone, and may be partially or fully substituted with fluorine.

7. The polymer according to claim 6 wherein the quinoline repeat units have the structure:

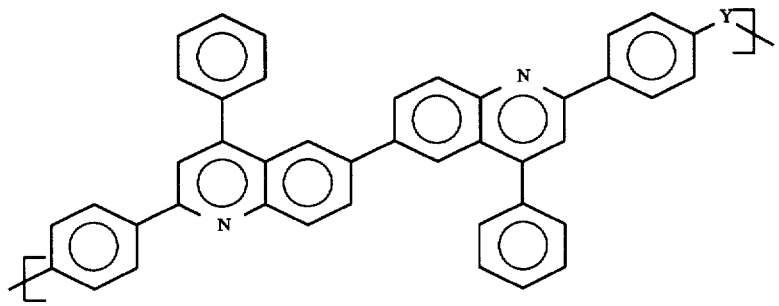

8. The polymer according to claim 6 wherein the quinoline repeat units have the structure:

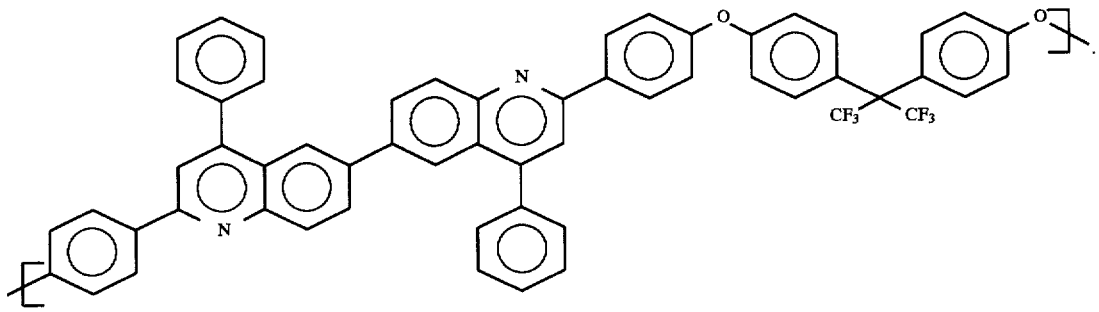

9. The polymer according to claim 1 wherein the quinoline repeat units have the structure:

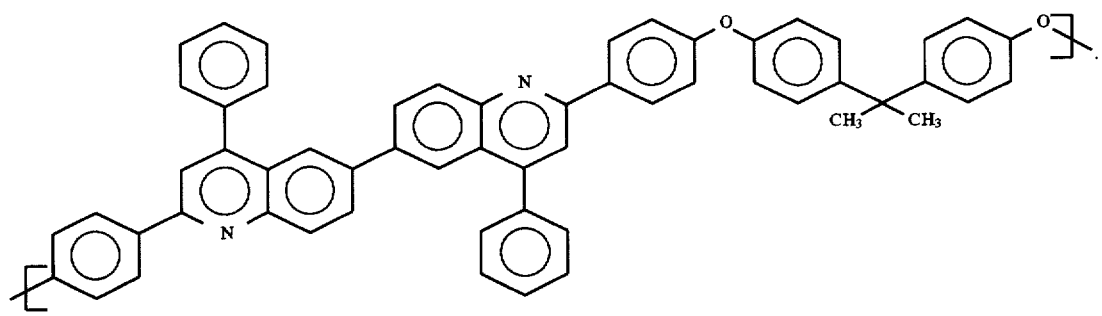

10. A polymer having the formula:

E"—(PQ)$_n$—E"

where PQ is a polyquinoline polymer repeat unit. n is 1 to 100,000. E" is an end group selected from —C≡CR, —Ar—C≡CR, —CH$_2$C≡CR, —Ar—OCH$_2$C≡CR, and —OCH$_2$C≡CR. R is H, alkyl, aryl or heteroaryl. Ar is arylene or heteroarylene, where Ar may be optionally substituted with alkyl, aryl, alkoxy, aryloxy, chloro, fluoro, fluoroalkyl, fluoroaryl, and nitro, and R may be optionally substituted with alkoxy, aryloxy, chloro, fluoro, fluoroalkyl, fluoroaryl, and nitro.

11. The polymer according to claim 10 comprising end groups selected from the group consisting of —OCH$_2$C≡CH, —OCH$_2$C≡CCH$_3$, —C≡CH, —C≡CC$_6$H$_5$, —C≡C—C$_6$H$_4$O$_6$CH$_5$, —C≡CCH$_3$.

12. The polymer according to claim 10 comprising end groups selected from the group consisting of —C$_6$H$_4$—C≡CH;

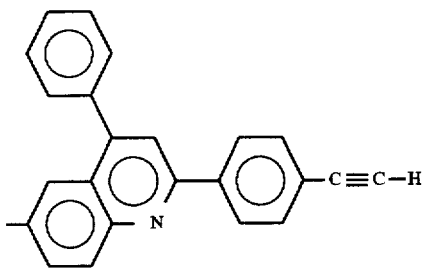

-continued

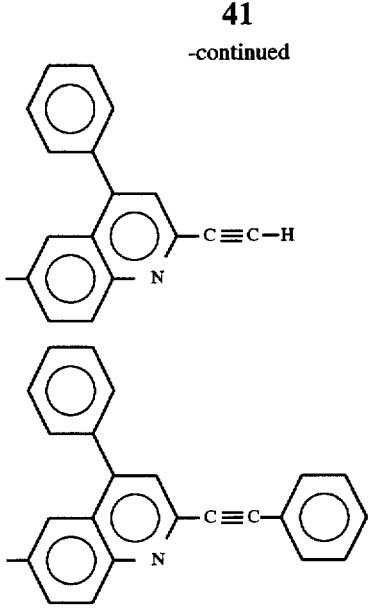

—C$_6$H$_4$—OCH$_2$C≡CH; —C$_6$H$_4$—OCH$_2$C≡CCH$_3$; and —C$_6$H$_4$—OCH$_2$C≡CC$_6$H$_5$.

13. The polymer according to claim 10 wherein Ar is selected from the group consisting of 1,4-phenylene, 1,3-phenylene, 2-methyl-1,4-phenylene, 1,4-naphthylene, 4,4'biphenylene, 2,4-pyridinediyl, 2,4-quinolinediyl, 2,6-quinolinediyl, 4-phenyl,-2,6-quinolinediyl, and 3,6-quinolinediyl.

14. The polymer according to claim 10 wherein the quinoline repeat units have the structure:

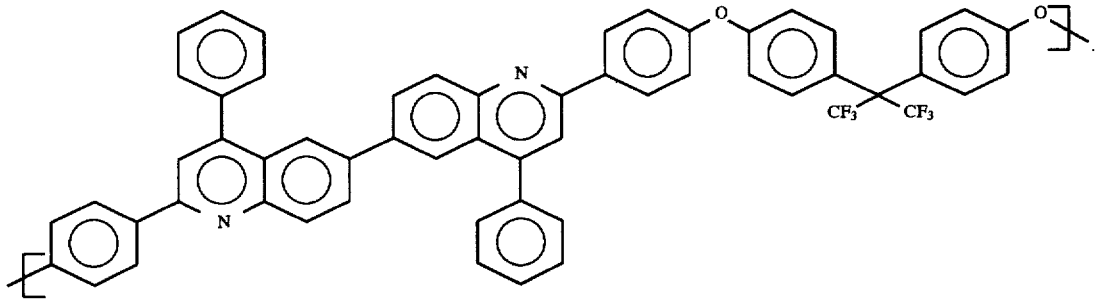

15. The polymer according to claim 10 wherein the quinoline repeat units have the structure:

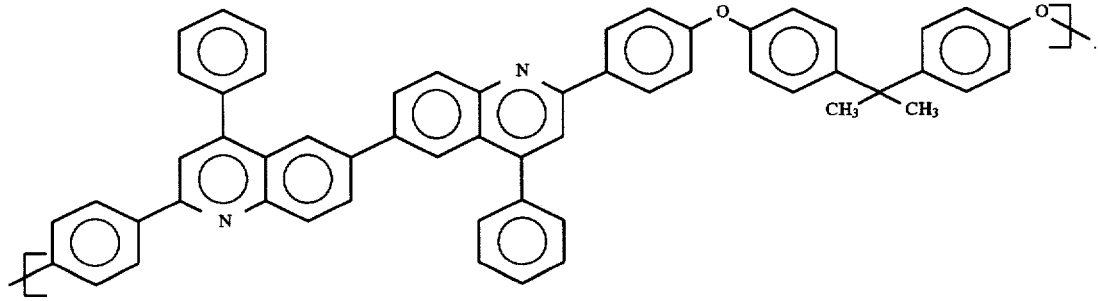

16. Cross-linked polyquinoline polymer compositions formed by heating a polymer of claim 10 above its T$_{ex}$.

17. A method for forming thermoset polyquinoline polymers compositions comprising heating a polymer of claim 10 above its T$_{ex}$.

18. The method according to claim 17 wherein the polymer is heated until at least half of the end groups have reacted.

19. The method according to claim 17 wherein the polymer is heated for a curing time determined by heating small (0.1 to 1 gram) samples of the polymer for various times and determining the exotherm area by differential scanning calorimetry, the curing time being the time necessary to reduce the exotherm area to 10% of the value for a sample that has not been heated.

20. The method according to claim 17 wherein the polymer is heated for a curing time determined by heating small (0.1 to 1 gram) samples of the polymer for various times and determining the exotherm area by differential scanning calorimetry, the curing time being the time necessary to reduce the exotherm area to 25% of the value for a sample that has not been heated.

21. The method according to claim 17 wherein the polymer is heated until it is insoluble in N-methylpyrrolidinone.

22. The method according to claim 17 wherein the polymer is heated under the application of pressure.

23. The method according to claim 22 wherein the polymer is heated under pressure in an autoclave.

24. The method according to claim 22 wherein the polymer is heated under pressure in a mold.

25. A method of forming solvent resistant films comprising coating a substrate with polymer compositions of claim 1 followed by heating the coated substrate above the T$_{ex}$ of said polymer composition.

26. The method of claim 25 wherein said polymer composition is spin coated onto a substrate from a solution of said polymer composition.

27. The method of claim 26 wherein the solution contains from 1% to 60% by weight solids.

28. The method of claim 26 wherein the solution contains from 10% to 30% by weight solids.

29. The method of claim 25 wherein the substrate is selected from the group consisting of aluminum, aluminum nitride, copper, diamond, quartz, silica, silicon, gallium arsenide, silicon carbide, gold, solder, and titanium; and where said substrate may have been previously coated with one or more layers of said polymer composition.

30. The method of claim 25 wherein said polymer composition is coated by spray coating a solution of said polymer composition.

31. The method of claim 25 wherein the substrate is a silicon wafer comprising preformed integrated circuits.

32. A method for preparation of thermosetting polyquinolines comprising a) allowing a bis-(fluoroquinoline) monomer to react with a partial molar excess of a diol monomer under conditions in which the diol is fully or partially deprotonated to thereby provide a hydroxy endcapped polymer, and b) allowing the hydroxy endcapped polymer formed in (a) to react with a propargyl halide under conditions in which the hydroxy endcapped polymer is fully or partially deprotonated.

33. The method of claim 32 wherein the hydroxy endcapped polymer formed in step (a) is isolated as a pure or semi-pure solid before performing step (b).

34. The method of claim 32 wherein the bis-(fluorquinoline) is 6,6'-bis[2-(4-fluorophenyl)-4-phenylquinoline].

* * * * *